(12) United States Patent
Kitamura et al.

(10) Patent No.: US 6,486,238 B1
(45) Date of Patent: Nov. 26, 2002

(54) HINDERED AMINE COMPOUND, RESIN COMPOSITION, POLYURETHANE FIBER AND PRODUCTION METHOD AND USE THEREOF

(75) Inventors: Kota Kitamura, Otsu (JP); Chihiro Oshimo, Otsu (JP); Genei Matsukawa, Tsuruga (JP); Futoshi Ishimaru, Otsu (JP)

(73) Assignee: Toyo Boseki Kabushiki Kaisha (JP)

( * ) Notice: Subject to any disclaimer, the term of this patent is extended or adjusted under 35 U.S.C. 154(b) by 0 days.

(21) Appl. No.: 09/468,005

(22) Filed: Dec. 20, 1999

(30) Foreign Application Priority Data

| Dec. 21, 1998 | (JP) | 10-363241 |
|---|---|---|
| Dec. 21, 1998 | (JP) | 10-363242 |
| Dec. 21, 1998 | (JP) | 10-363243 |

(51) Int. Cl.[7] ............................................. C08K 5/3435
(52) U.S. Cl. ............................ 524/100; 8/590; 524/102; 524/119; 524/120; 525/123; 525/125; 525/127; 526/263; 526/265; 546/188; 546/190
(58) Field of Search ............................ 526/263, 265; 524/100, 119, 120, 102; 546/188, 190; 525/123, 125, 127; 8/590

(56) References Cited

U.S. PATENT DOCUMENTS

| 3,053,878 | A | * | 9/1962 | Friedman et al. ............ 524/120 |
| 3,558,266 | A | * | 1/1971 | Kleemann et al. ............. 8/590 |
| 3,640,928 | A | | 2/1972 | Murayama et al. |
| 3,705,166 | A | * | 12/1972 | Murayama et al. ......... 524/100 |
| 4,140,673 | A | * | 2/1979 | Lachmann et al. ......... 546/186 |
| 4,210,612 | A | * | 7/1980 | Karrer ........................ 526/263 |
| 4,276,401 | A | * | 6/1981 | Karrer ........................ 526/263 |
| 4,294,949 | A | | 10/1981 | Karrer ........................ 526/262 |
| 4,308,362 | A | * | 12/1981 | Wiezer et al. ............... 525/328 |
| 4,369,274 | A | * | 1/1983 | Thomas ...................... 526/265 |
| 4,983,737 | A | * | 1/1991 | Ravichandran et al. ..... 546/188 |
| 5,260,135 | A | | 11/1993 | Corrigan et al. |
| 5,405,891 | A | * | 4/1995 | Pitteloud .................... 524/102 |
| 5,504,211 | A | * | 4/1996 | Aumueller ................... 544/190 |
| 5,973,040 | A | * | 10/1999 | Krause et al. .............. 524/143 |
| 6,103,796 | A | | 8/2000 | Staniek et al. |
| 6,201,047 | B1 | * | 3/2001 | Avar et al. .................. 546/187 |

FOREIGN PATENT DOCUMENTS

| CA | C1338 946 | 2/1997 |
| DE | 44 18 080 A1 | 12/1994 |
| EP | 03 89 423 | 9/1990 |
| EP | 0 632 147 A2 | 6/1994 |
| EP | 0 33 774 4 | 8/1995 |
| EP | 03 01 092 | 10/1997 |
| EP | 03 37 744 | 10/1998 |
| JP | 53-129 4 | 1/1978 |
| JP | 53-393 95 | 4/1978 |
| JP | 1-26 140 9 | 10/1989 |
| JP | 5-1 127 25 | 5/1992 |
| JP | 5-1 559 77 | 6/1993 |
| JP | 5-2 627 70 | 10/1993 |
| JP | 6-20 714 2 | 7/1994 |
| JP | 6-2 07 142 | 7/1994 |
| JP | 6-2 40 220 | 8/1994 |
| JP | 6-2 64 029 | 9/1994 |
| JP | 7-49 453 | 5/1995 |
| JP | 7-57 857 | 6/1995 |
| JP | 9-3 133 | 1/1997 |
| JP | 10-4 61 41 | 2/1998 |

OTHER PUBLICATIONS

Patent Abstracts of Japan, vol. 13, No. 515 (C–655), (Nov. 17, 1989) & JP 01 207350 A (ToyOBO Co., Ltd)., (Aug. 21, 1989).

* cited by examiner

*Primary Examiner*—Peter Szekely
(74) *Attorney, Agent, or Firm*—Kenyon & Kenyon

(57) ABSTRACT

A hindered amine compound having thesolubility in an acidic solution of $5.0 \times 10^{-3}$ eq./liter or less comprising at least two specific organic groups in a specific weight ratio in a molecule, or at least two specific monomeric units, which can be used as a stabilizer of a resin.

37 Claims, No Drawings

HINDERED AMINE COMPOUND, RESIN COMPOSITION, POLYURETHANE FIBER AND PRODUCTION METHOD AND USE THEREOF

BACKGROUND OF THE INVENTION

1. Field of the Invention

The present invention relates to a hindered amine compound, a resin composition comprising a hindered amine compound which achieves stabilizing effects (resistance to $NO_x$, light stabilization, etc.) even after various processing processes, a resin composition comprising such a hindered amine compound which is sufficiently stabilized even after various processing processes, a polyurethane resin composition and fiber comprising such a hindered amine compound which is sufficiently stabilized even after various processing processes, and a method for the preparation of such a polyurethane fiber.

Furthermore, the present invention relates to a polyurethane resin composition and fiber which is stabilized against discoloration caused with $NO_x$, and a method for the preparation of such a polyurethane fiber.

In addition, the present invention relates to a stretch fabric or knit comprising a polyurethane fiber and a non-stretch fiber such as a polyester fiber, a polyamide fiber, a cellulose fiber, etc.

2. Prior Art

Polyalkyl-substituted piperidine derivatives are called hindered amine compounds, and widely used as stabilizers of various resins since they have high stabilizing effects on resin materials.

Hindered amine compounds are usually used to suppress the degradation caused by light (UV rays). Hindered amine compounds of various structures are widely used depending on the kinds of resins to be stabilized, purposes, applications, etc.

Polyurethane resins are more easily deteriorated by various factors than other resins, and it is essential for polyurethane resins to compound stabilizers. Among the applications of polyurethane resin compositions, a polyurethane fiber particularly deteriorates since it has a large surface area per a unit weight.

Among the causes for the deterioration of polyurethane, even a slight amount of nitrogen oxides ($NO_x$) discolor the polyurethane. Thus, it is highly desired to develop an effective stabilizer against $NO_x$. Among others, hindered amine compounds have a high effect to suppress the discoloration of polyurethane with $NO_x$, and thus various types of hindered amine compounds have been developed.

However, even polyurethane products which are stabilized by the compounding of hindered amine compounds often lose the stabilizing effects of the hindered amine compounds after secondary processing. One example of such a case is dyeing of polyurethane fibers. Fibers can be dyed by various methods depending on the kinds of fibers and applications of dyed fibers. In particular, fibers are often treated in an acidic aqueous solution. Hindered amine compounds form salts with acids in the acidic aqueous solution, since they are basic compounds. Thus, it is one reason why the stabilizing effects of the hindered amine compounds are lost that the hindered amine compounds form water-soluble salts and liberate from the fibers. Such a phenomenon is remarkable with low molecular weight hindered amine compounds, although high molecular weight hindered amine compounds having a molecular weight of several thousand to several ten thousand may encounter the same phenomenon. Therefore, the increase of the number of hindered amino groups in a molecule to improve the stabilizing effects lead to the easy liberation of the hindered amine compound by the treatment in the acidic solution. That is, the concentration of the hindered amino groups in a molecule has a close relationship with the liberation of a hindered amine compound from fibers, and the prevention of the liberation of hindered amine compounds is incompatible with the high stabilizing effects.

To ultimately prevent the liberation of hindered amine compounds, many literatures propose the reaction of the hindered amine compounds with polymers constituting resins. For example, the reaction of hindered amine compounds with polyurethane is disclosed in JP-A-53-1294, JP-A-53-39395, JP-A-5-155977, etc. However, when hindered amine compounds are reacted with resin polymers as disclosed in JP-A-53-1294 and JP-A-53-39395, the physical properties of the resins more or less deteriorate in comparison with unreacted resins. For example, when hindered amino groups are introduced at polymer chain ends using a hindered amine compound as a chain terminating agent, the increase of the number of terminal groups derived from the hindered amine compound to improve the stabilizing effects inevitably lead to the decrease of the molecular weight of the polymer. Accordingly, the improvement of the stabilizing effects by the increase of the number of terminal groups derived from hindered amine compounds is essentially incompatible with the improvement of physical properties by the increase of the molecular weight. Thus, it is impossible to increase both the physical properties and the stabilizing effects.

When a compound having a hindered amino group is incorporated as a side chain in a polymer chain, the molecular weight of the polymer is not influenced by the amount of the incorporated hindered amine compound, but the synthesis of the hindered amine compound and the polymerization of the polymer are complicated.

Even if polymers having hindered amino groups as side chains are prepared, the presence of bulky groups such as hindered amino groups in side chains has influences on the interaction of the polymer molecules and in turn on the physical properties of the polymers.

Many proposals have been made on the reaction of hindered amine compounds with polymers constituting resins other than polyurethane. For example, JP-A-5-262870, JP-A-6-207142, JP-A-6-240220 and JP-A-6-264029 disclose stabilized resins which are obtained by copolymerizing a polymerizable hindered amine monomeric compound having a carbon-carbon double bond with a polymerizable monomer constituting the resins. The polymerizable hindered amine monomeric compounds which are proposed in these Japanese patent applications are relatively easily copolymerized with the monomer constituting the resins, but the kinds of the resins to be copolymerized are limited to those of vinyl monomers.

Many proposals have been made on the use of copolymers of polymerizable hindered amine monomeric compounds and other polymerizable monomers as stabilizers of resins (see, for example, JP-A-5-112725, JP-A-9-3133, JP-A-10-46141, etc.)

These proposals can prevent the liberation of the hindered amine compounds by heat, or with neutral water or hot water. However, these proposals are not intended to prevent the liberation of the hindered amine compounds by the treatment with acids. Thus, they have the same drawbacks as those for the above high molecular weight hindered amine compounds.

JP-A-10-46141 discloses a polymer or a copolymer of a polymerizable hindered amine monomeric compound as a stabilizer which suppresses the yellowing of clothes during storage. However, the disclosed invention does not shape a compound as a product after compounding a hindered amine compound in a resin. Rather, the hindered amine compound is attached to shaped products such as finished clothes by post-processing. This process can stabilize the finished products, but the stability of intermediate products which are being processed prior to finishing cannot be improved. In particular, in the case of clothes, such a drawback is not negligible, since the processing from fibers to the finished products often takes a long time.

In the case of resins such as polyurethane which are particularly easily degraded, the resins themselves should have stability. Thus, stabilizers are compounded even in primary products prior to final products, and they should not lose stabilizing properties in the post-processing processes such as secondary processing.

Polyurethane is prepared from a polyisocyanate, a polymer diol having a relatively low molecular weight and a polyfunctional active hydrogen compound having a low molecular weight, and used in awide varietyof applications such as foams, elastomers, paints, synthetic leather, fibers, etc. because it has good mechanical properties and it is easily processed. In particular, polyurethane prepared using an aromatic isocyanate such as 4,4'-diphenylmethane diisocyanate as a polyisocyanate is broadly used since it has excellent mechanical properties.

However, polyurethane prepared from aromatic isocyanates has a drawback that it is heavily discolored with $NO_x$. $NO_x$ is contained in combustion gas or exhaust gas, and it discolors polyurethane even in a very small amount. Therefore, the suppression of discoloration of polyurethane caused with $NO_x$ has been discussed for a long time. For example, phosphite ester antioxidants, aliphatic amine derivatives and hydrazine derivative are known as stabilizers which suppress the discoloration of polyurethane caused with $NO_x$. Among them, the phosphite ester antioxidants, and hindered amine compounds as aliphatic amine derivatives are generally used since they achieve particularly high stabilizing effects.

However, the phosphite ester antioxidants and hindered amine compounds should be used in combination with phenol antioxidants to impart processing stability and heat resistance to polyurethane, since they have low effects to suppress thermal oxidation of polyurethane. It is known to use three stabilizers, that is, a phenol antioxidant, a phosphite ester antioxidant and a hindered amine compound, and the mixed stabilizer has a remarkable effect to prevent the discoloration of polyurethane. However, when a polyurethane resin composition containing such a mixed stabilizer is subjected to a secondary processing such as dyeing of fibers, the stabilizing effects of the mixed stabilizer are often greatly impaired. Such a polyurethane resin composition which loses the stabilizing effects by the secondary processing has a serious drawback since it has a large risk that a final product suffers from disoloration or deterioration.

Fabrics or knits comprising a polyurethane fiber and a non-stretch fiber such as a polyester fiber, a polyamide fiber or a cellulose fiber have good stretch properties. Thus they are used in a wide variety of applications, for example, the legs of panty hoses or socks; foundation garments or undergarments such as brassieres, girdles, bodysuits, etc.; sports wears such as swimming suits, leotards, etc.; outer garments such as ski pants, stretch denims, etc.; and the like.

Furthermore, such fabrics and knits can be used in medical applications such as stretch bandages, stretch corsets, base cloths of stretch tapes, athletic supporters, etc.; base cloths of stretch boots; and the like.

However, since polyurethane has the above-described drawbacks, the stabilizing effects of stabilizers are often severely impaired, when stretch fabrics or knits comprising polyurethane fibers containing conventional stabilizers are dyed. Therefore, stretch fabrics or knits comprising such polyurethane fibers or their final products have problems that they are yellowed or deteriorated on exposure to an atmosphere containing $NO_x$.

As described above, hindered amine compounds sometimes lose their stabilizing effects due to secondary processing such as dyeing, although they exhibit high stabilizing effects as stabilizers of resins.

Hitherto, no hindered amine compound has been provided, that is used as a stabilizer of resins and fibers, in particular, fibers which should be dyed under acidic conditions, and can exhibits satisfactory stabilizing effects without deteriorating the inherent properties of the resins even after the processing.

When hindered amine compounds are chemically bonded with polymers constituting resins, the obtained resins have good stability even after secondary processing, but their physical properties are greatly deteriorated.

Thus, it is highly desired to develop a stabilizer which can be compounded in a resin as a discrete stabilizer from the polymer constituting the resin, and achieves good stabilizing effects not only on resin materials but also on processed products which have been subjected to various processing steps such as dying. In particular, in the case of polyurethane, the intermolecular interaction greatly contributes to its good physical properties. Therefore, the introduction of a different structure in polymer chains largely deteriorates the physical properties, and the polyurethane having such a different structure in the polymer chain is easily discolored with $NO_x$. Therefore, the above type of a stabilizer is highly important.

A polyurethane resin composition containing a phosphite ester antioxidant, a phenol antioxidant and a hindered amine compound has high stability against degradation, but the stabilizing effects of the mixed stabilizer are sometimes lost after processing.

SUMMARY OF THE INVENTION

One object of the present invention is to provide a hindered amine compound which can be compounded in a resin as a discrete stabilizer from the polymer constituting the resin without deteriorating the properties of the resin, and achieves good stabilizing effects (e.g. resistance to $NO_x$, light stabilization, etc.) on the resin even after the resin is subjected to various processing steps such as dying.

Another object of the present invention is to provide a polyurethane resin composition or fiber which has good light stability and is stabilized against discoloration caused by $NO_x$ not only in the form of an intermediate product but also in the form of a final product after various processing such as dyeing.

According to the first aspect of the present invention, there is provided a hindered amine compound having, in amolecule, at least one organic group (A1) selected from the group consisting of a monovalent organic group of the formula (1):

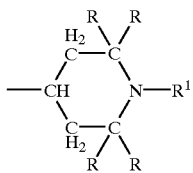
(1)

in which R is an alkyl group having 1 to 10 carbon atoms, which may optionally be substituted, and $R^1$ is a hydrogen atom, an alkyl group having 1 to 10 carbon atoms, which may optionally be substituted, or an alkoxy group having 1 to 10 carbon atoms, and a divalent organic group of the formula (2):

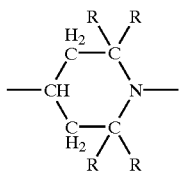
(2)

in which R is the same as defined above, wherein
(a) the number of the organic group (A1) is at least 1.3 moles per 1 kg of the hindered amine compound, and
(b) the solubility of the hindered amine compound is $5.0 \times 10^{-3}$ eq./liter or less in an acidic solution.

According to the second aspect of the present invention, there is provided a hindered amine compound having, in a molecule, at least one organic group (A2) selected from the group consisting of a monovalent organic group of the formula (3):

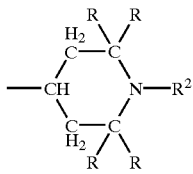
(3)

in which R is an alkyl group having 1 to 10 carbon atoms, which may optionally be substituted, and $R^2$ is a hydrogen atom, an alkyl group having 1 to 10 carbon atoms, which may optionally be substituted, or an alkoxy group having 1 to 10 carbon atoms, and a divalent organic group of the formula (4):

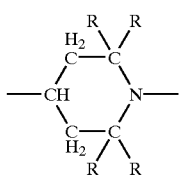
(4)

in which R is the same as defined above, and at least one organic group (C1) selected from the group consisting of a cycloalkyl group having 5 to 10 carbon atoms and a cycloalkylene group having
5 to 10 carbon atoms,
wherein the weight percentages $W_{A2}$ and $W_{C1}$ of the organic groups (A2) and (C1), respectively, satisfy the following formulas (I) and (II):

$$40 \leq W_{A2} + W_{C1} \leq 70 \quad (I)$$

$$0.6 \leq W_{A2}/W_{C1} \leq 3 \quad (II)$$

According to the third aspect of the present invention, there is provided a hindered amine compound obtained by copolymerizing at least one polymerizable hindered amine monomeric compound (A3) of the formula (5):

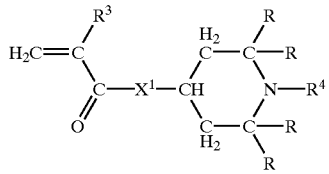
(5)

in which R is an alkyl group having 1 to 10 carbon atoms, which may optionally be substituted, $R^3$ is a hydrogen atom or a methyl group, $R^4$ is a hydrogen atom, an alkyl group having 1 to 10 carbon atoms, which may optionally be substituted, or an alkoxy group having 1 to 10 carbon atoms, and $X^1$ is a —O— group or a —NH— group, and at least one polymerizable monomer (C2) of the formula (6)

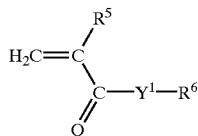
(6)

in which $R^5$ is a hydrogen atom or a methyl group, $R^6$ is a cycloalkyl group having 5 to 10 carbon atoms, and $Y^1$ is a —O— group or a —NH— group, wherein the weight percentages $W_{A3}$ and $W_{C2}$ of the components (A3) and (C2), respectively, satisfy the following formulas (III) and (IV):

$$80 \leq W_{A3} + W_{C2} \leq 100 \quad (III)$$

$$0.5 \leq W_{A3}/W_{C2} \leq 2.3 \quad (IV)$$

According to the fourth aspect of the present invention, there is provided a hindered amine compound obtained by copolymerizing at least one polymerizable hindered amine monomeric compound (A4) of the formula (7):

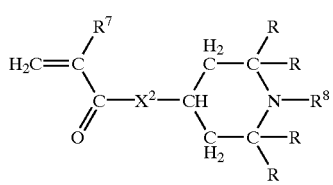
(7)

in which R is an alkyl group having 1 to 10 carbon atoms, which may optionally be substituted, $R^7$ is a hydrogen atom or a methyl group, $R^8$ is a hydrogen atom, an alkyl group having 1 to 10 carbon atoms, which may optionally be substituted, or an alkoxy group having 1 to 10 carbon atoms, and $X^2$ is a —O— group or a —NH— group, and at least one polymerizable monomer (D1) of the formula (8):

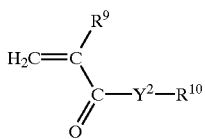

(8)

in which $R^9$ is a hydrogen atom or a methyl group, $R^{10}$ is a straight or branched alkyl group having 10 to 30 carbon atoms, and $Y^2$ is a —O— group or a —NH— group, wherein the weight percentages $W_{A4}$ and $W_{D1}$ of the components (A4) and (D1), respectively, satisfy the following formulas (V) and (VI):

$$80 \leq W_{A4} + W_{D1} \leq 100 \quad (V)$$

$$8.3 \leq W_{A4}/W_{D1} \leq 2.3 \quad (VI)$$

According to the fifth aspect of the present invention, there is provided a hindered amine compound of the formula (9):

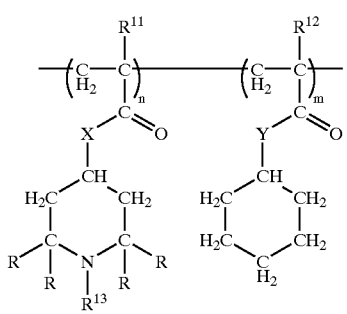

(9)

in which R is an alkyl group having 1 to 10 carbon atoms, which may optionally be substituted, $R^{11}$ and $R^{12}$ are the same or different and each a hydrogen atom or a methyl group, $R^{13}$ is a hydrogen atom, an alkyl group having 1 to 10 carbon atoms, which may optionally be substituted, or an alkoxy group having 1 to 10 carbon atoms, X and Y are the same or different and each a —O— group or a —NH— group, and n and m are positive integers satisfying the formula: $0.35 \leq n/m \leq 1.75$, and the sum of n and m is from 2 to 10000.

According to the sixth aspect of the present invention, there is provided a hindered amine compound of the formula (10):

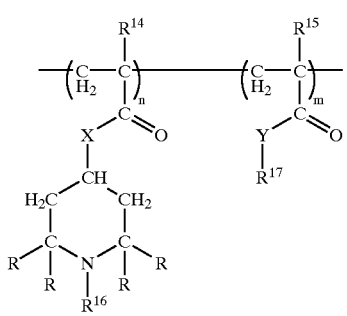

(10)

in which R is an alkyl group having 1 to 10 carbon atoms, which may optionally be substituted, $R^{14}$ and $R^{15}$ are the same or different and each a hydrogen atom or a methyl group, $R^{16}$ is a hydrogen atom, an alkyl group having 1 to 10 carbon atoms, which may optionally be substituted, or an alkoxy group having 1 to 10 carbon atoms, $R^{17}$ is a straight or branched alkyl group having 10 to 30 carbon atoms, X and Y are the same or different and each a —O— group or a —NH— group, and n and m are positive integers satisfying the formula: $0.65 \leq n/m \leq 2.50$, and the sum of n and m is from 2 to 10000.

In a preferred embodiment, at least a part of the hindered amino groups of the above hindered amine compounds of the present invention form salts with at least one compound selected from the group consisting of organic carboxylic acids, carbon dioxide, phosphoric acid, phosphate esters, phosphorous acid and phosphite esters.

According to the seventh aspect of the present invention, there is provided a resin composition comprising at least one of the hindered amine compounds according to the first to sixth aspects of the present invention.

In a preferred embodiment, the above resin composition contains a phosphite ester antioxidant.

In another preferred embodiment, the resin in the above resin composition is polyurethane.

In the eighth aspect of the present invention, there is provided a resin composition comprising polyurethane, a phenol antioxidant, a phosphite ester antioxidant, and at least one of the hindered amine compounds according to the first to sixth aspects of the present invention, in which the amount of the phenol antioxidant is preferably from 0.1 to 2 wt. %, the amount of the phosphite ester is preferably from 0.1 to 2 wt. %, and the amount of the hindered amine compound is from 0.5 to 5 wt. %, based on the weight of polyurethane.

In a preferred embodiment, the above phosphite ester antioxidant is a hydrogenated bisphenol A-pentaerithritol phosphite polymer of the formula (11):

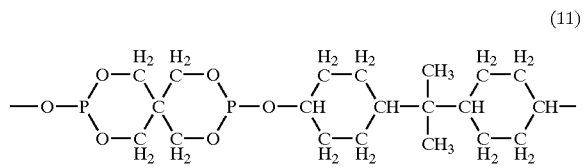

(11)

In another preferred embodiment, the above phenol antioxidant is aphenol compound which has the chemical structure of the formula (12):

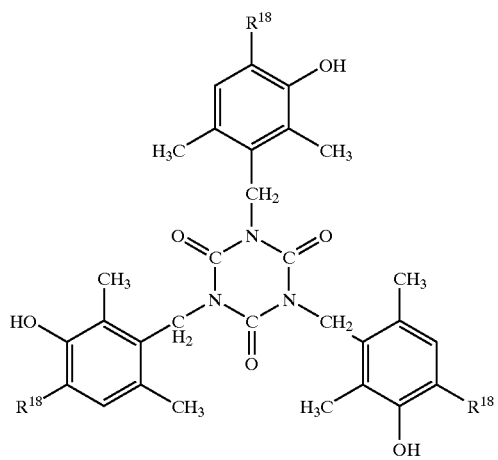

(12)

whereom $R^{18}$ is a tert.-butyl group, a sec-butyl group or a neopentyl group.

According to the ninth aspect of the present invention, there is provided a polyurethane fiber prepared from the polyurethane resin composition according to the seventh and eighth aspects of the present invention.

According to the tenth aspect of the present invention, there is provided a method for the production of a polyurethane fiber comprising the step of spinning the polyurethane resin composition according to the seventh and eighth aspects of the present invention.

According to the eleventh aspect of the present invention, there is provided a stretch fabric or knit comprising a polyurethane fiber according to the ninth aspect of the present invention, and a non-stretch fiber.

In a preferred embodiment, the above non-stretch fiber is at least one fiber selected from the group consisting of a polyester fiber, a polyamide fiber and a cellulose fiber.

In another preferred embodiment, the polyurethane fiber is a bare fiber or a composite fiber.

DETAILED DESCRIPTION OF THE INVENTION

The mono- or divalent organic group (A1) in the hindered amine compound according to the first aspect of the present invention is at least one organic group selected from the group consisting of a monovalent organic group of the formula (1) and a divalent organic group of the formula (2).

When the organic group (A1) is a monovalent one, it is preferably bonded at the 4-position of the piperidine ring to other site of the compound.

R in the formula (1) or (2) is a substitutedor unsubstituted alkyl group having 1 to 10 carbon atoms, preferably 1 to 4 carbon atoms, and more preferably methyl group.

$R^1$ in the formula (1) is a hydrogen atom, a substituted or unsubstituted alkyl group having 1 to 10 carbon atoms, or an alkoxyl group having 1 to 10 carbon atoms. Among them, a hydrogen atom or an alkyl group having 1 to 4 carbon atoms is preferred from the viewpoint of stabilizing effects, and a hydrogen atom or a methyl group is more preferable.

When the organic group (A1) is a divalent one, it is preferably bonded at the 1- and 4-positions of the piperidine ring to other sites of the compound. Preferred examples of the organic group (A1) include compounds of the following formulas (13) to (15):

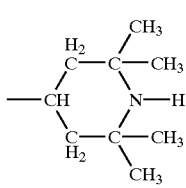

(13)

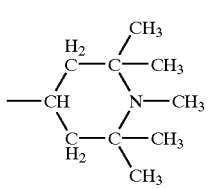

(14)

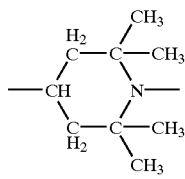

(15)

The organic group (A1) may be a single organic group or a mixture of two or more organic groups, insofar as the above definitions are met. In addition, the organic group (A1) may be a mixture of at least one monovalent organic group and at least one divalent organic group. In particular, the organic group (A1) is preferably an organic group of the formula (13).

The number of the organic groups (A1) is at least 1.3 moles per 1 kg of the hindered amine compound. When the number of the organic groups (A1) is less than 1.3 moles, the stabilizingeffects may decrease since the number of effective sites of the compound, which contribute to the stabilization, becomes too small. Furthermore, as the number of the organic groups (A1) decreases, the increased amount of the hindered amine compound should be added to a resin composition to achieve the same effects, which is unfavorable from the viewpoint of the costs.

The number of the organic group (A1) is preferably at least 2.0 moles per 1 kg of the hindered amine compound from the viewpoint of stabilizing effects.

Herein, the solubility of a hindered amine compound in an acidic solution is measured as follows:

Measurement of an Amount of a Base per 1 kg of a Hindered Amine Compound 0.0200 g of a hindered amine compound is accurately weighed. When a hindered amine compound is in the form of a solution, the hindered amine compound is once recovered from the solution and then weighed, or the weight of the solution is weighed so that the weight of the hindered amine compound reaches the determined weight. To recover the hindered amine compound from the solution, any known method such as reprecipitation, recrystallization, evaporation of a solvent, etc. may be used.

Then, the weighed hindered amine compound is dissolved in 100 ml of a solvent. A used solvent is preferably a solvent in which the hindered amine compound is well dissolved, and which does not have a basicity, and is miscible with water.

Examples of such a solvent include lower alcohols (e.g. methanol, ethanol, propanol, etc.), amides (e.g. N,N-dimethylformamide, N,N-dimethylacetamide, etc.), ethers (e.g. tetrahydrofuran, dioxane, etc.), and the like. From these solvents, a solvent which can dissolve therein a hindered amine compound to be tested is suitably selected.

The solution of the hindered amine compound is then subjected to neutralization titration with a 1/100 N hydrochloric acid using potentiometric titration equipment (COMTITE-980 available from HIRANUMA Industries, Ltd.), a glass electrode (GE-101 available from HIRANUMA Industries, Ltd.) and a reference electrode (RE-101 available from HIRANUMA Industries, Ltd.).

The amount of a base ($B_A$; unit: eq/kg) per 1 kg of the hindered amine compound is calculated according to he following equation:

$$B_A = (V \times F \times 10^{-2})/0.0200 \quad \text{(VII)}$$

in which V is a titer (ml) and F is a factor of the 1/100 N hydrochloric acid.

Preparation of an Acidic Solution 1.200 g of acetic acid, and 0.250 g of anhydrous sodium acetate are accurately weighed, and dissolved in 1 liter of pure water in a graduated flask.

Measurement of Solubility of a Hindered Amine Compound in an Acidic Solution

Using a base amount per 1 kg of a hindered amine compound, the weight ($W_A$; unit: g) of the hindered amine compound for the solubility measurement is calculated so that the total base amount is $5.0 \times 10^{-5}$ mole according to the following equation:

$$W_A = (5 \times 10^{-2})/B_A \quad (VIII)$$

in which $B_A$ is the base amount (eq/kg) per 1 kg of the hindered amine compound.

The hindered amine compound of the weight calculated according to equation (VIII) is accurately weighed, and charged in a glass ampoule together with 5 ml of the above prepared acidic solution and then sealed. The ampoule is heated at 100° C. for 1 hour, cooled and then unsealed.

Three milliliters of the liquid in the ampoule, which has been filtered through a 0.45um filter, and ml of a 1/10 N aqueous sodium hydroxide solution were dissolved in 100 ml of a solvent. The solvent may be the same as that used in the above measurement of the base amount.

The mixed solution is subjected to neutralization titration with a 1/100 N hydrochloric acid using potentiometric titration equipment. As a blank, 3 ml of distilled water containing $3.6 \times 10^{-3}$ g of acetic acid and $0.75 \times 10^{-3}$ g of anhydrous sodium acetate and 1 ml of a 1/10 N aqueous sodium hydroxide solution were dissolved in 100 ml of the solvent, and then subjected to the neutralization titration.

The end point of the titration is a time when all the bases (the hindered amine compound, sodium acetate and sodium hydroxide) are titrated, and then a titer is determined.

The solubility ($S_A$; unit: eq/liter) of the hindered amine compound in the acidic solution is calculated as the amount of the base dissolved in 1 liter of the acidic solution according to the following equation:

$$S_A = (V_S - V_B)/300 \quad (IX)$$

in which $V_S$ is a titer (ml) for 3 ml of the sample solution and $V_B$ is a titer for 3 ml of the blank solution.

The hindered amine compound according to the first aspect of the present invention has a solubility of no larger than $5.0 \times 10^{-3}$ eq./liter, when the solubility is measured as described above. The smaller solubility is more preferred. The hindered amine compound has better properties, when its solubility is $2.5 \times 10^{-3}$ eq/liter or less.

The organic group (A2) of the hindered amine compound according to the second aspect of the present invention is at least one mono- or divalent organic group selected from the group consisting of a monovalent organic group of the formula (3) and a divalent organic group of the formula (4).

R in the formula (3) or (4) is a substitutedor unsubstituted alkyl group having 1 to 10 carbon atoms, preferably 1 to 4 carbon atoms, and more preferably methyl group.

$R^2$ in the formula (3) is a hydrogen atom, a substituted or unsubstituted alkyl group having 1 to 10 carbon atoms, or an alkoxyl group having 1 to 10 carbon atoms. Among them, a hydrogen atom or an alkyl group having 1 to 4 carbon atoms is preferred from the viewpoint of stabilizing effects, and a hydrogen atom or a methyl group is more preferable.

When the organic group (A2) is a divalent one, it is preferably bonded at the 1- and 4-positions of the piperidine ring to other sites of the compound. Preferred examples of the organic group (A2) include compounds of the above formulas (13) to (15).

The organic group (A2) may be a single organic group or a mixture of two or more organic groups, insofar as the above definitions are met. In addition, the organic group (A2) may be a mixture of at least one monovalent organic group and at least one divalent organic group. In particular, the organic group (A2) preferably consists of the above structure (9).

The organic group (C1) in the hindered amine compound according to the second aspect of the present invention is at least one mono- or divalent organic group selected from the group consisting of a cycloalkyl group having 5 to 10 carbon atoms and a cycloalkylene group having 5 to 10 carbon atoms.

When the number of the carbon atoms in the organic group is small, the effect exerted by each group is small, so that the resin composition is not sufficiently stabilized after processing. When the number of carbon atoms is too large, the number of groups decreases, and thus the effects exerted by the whole groups decreases so that the sufficient stabilizing effects after the processing of a resin composition cannot be attained.

Preferably, the organic group (C1) is a cycloalkyl group having 5 to 10 carbon atoms.

A cycloalkyl group used herein means a group having at least one closed ring consisting of a plurality of carbon atoms which are covalently bonded. When one cycloalkyl group has two or more rings, the rings may share some carbon atoms. In a cycloalkyl group, each ring has at least 3 carbon atoms, preferably 5 or 6 carbon atoms.

A cycloalkyl group may have at least one straight or branched alkyl group having 1 to 5 carbon atoms as a substituent. Although the number of the substituent alkyl groups on a cycloalkyl group is not limited, the total number of carbon atoms of the substituent alkyl groups is generally 5 to 10. Preferably, a cycloalkyl group consists of carbon and hydrogen atoms.

Furthermore, a cycloalkyl group has only covalent bonds, and neither a double bond nor a triple bond, from the viewpoint of the stabilizing effects.

All the organic groups (C1) may the same groups, while they may comprise two or more different groups.

Preferred examples of the organic group (C1) are the groups of the following formulas (16) to (25):

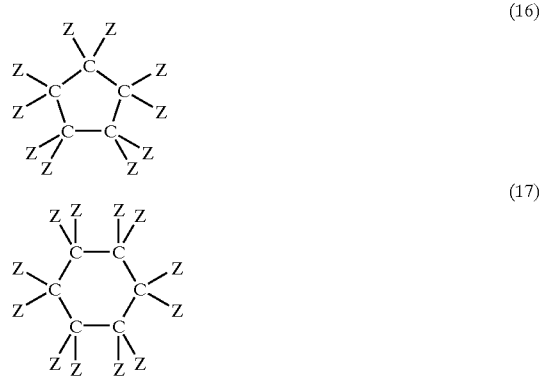

-continued

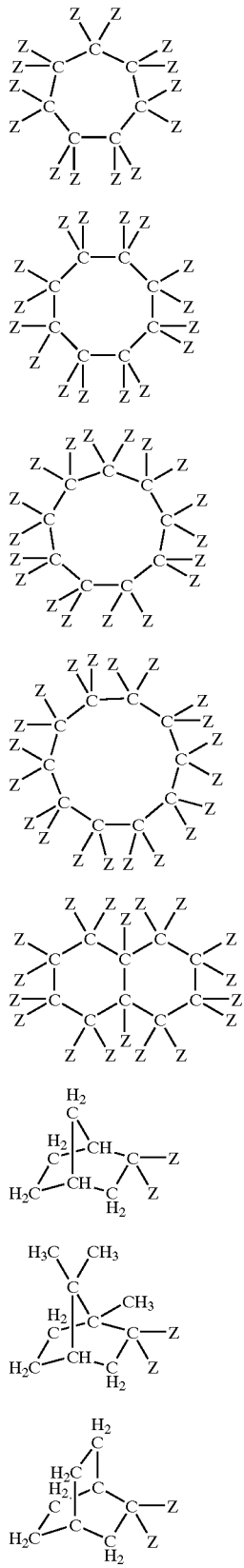

wherein Z is a hydrogen atom, a straight or branched alkyl group having 1 to 5 carbon atoms, or a bonding site which is bonded with other site of a hindered amine compound, provided that the total number of carbon atoms in each formula does not exceed 10, and the number of bonding sites is 1 or 2.

Among them, a cyclopentyl group, a cyclohexyl group, a cycloheptyl group, a cyclooctyl group, a cyclononyl group, a cyclodecyl group, a norbornyl group, a bornyl group, an isobornyl group and a decahydronaphthyl group are preferred. In particular, a cyclohexyl group and a isobornyl group are preferred.

The hindered amine compound according to the second aspect of the present invention has at least one organic group (A2) and atleastoneorganicgroup (C1) inonemolecule. Thetotalweight percentage of the organic group (A2) and the organic group (C1) in the hindered amine compound is preferably from 40 wt. % to 70 wt. %. When the total weight percentage of the two kinds of the organic groups is less than 40 wt. %, the hindered amine compound has low stabilizing effects, so that a large amount of the hindered amine compound should be compounded in a resin composition, whichisunfavorable fromtheviewpointof the costs. When the total weight percentage of the two kinds of the organic groups exceeds 70 wt. %, the stabilizing effects after the processing of a resin composition deteriorate, although the stabilizingeffectsprior to theprocessingrelativelyincrease. The total weight percentage of the two kinds of the organic groups is preferably from 50 wt. % to 60 wt. %.

In addition, a ratio of the weight percentage of the organic group (A2) to that of the organic group (C1) is preferably in the range between 0.6 and 3. When this ratio is less than 0.6, the stabilizing effects prior to the processing of a resin composition decrease, while when this ratio exceeds 3, the stabilizing effects after the processing of a resin composition deteriorate. This ratio is preferably in the range between 1.0 and 2.5.

The weight percentage of the organic group (A2) or the organic group (C1) is expressed in terms of a ratio of the formula weight of each organic group to the molecular weight of the hindered amine compound. When the hindered amine compound is a polymeric compound comprising repeating units, the weight percentage of each organic group can be calculated with the repeating units.

The hindered amine compound according to the third aspect of the present invention is obtained by copolymerizing at least one polymerizable hindered amine monomeric compound (A3) of the formula (5) and at least one polymerizable monomer (C2) of the formula (6). In addition, the weight percentages $W_{A3}$ and $W_{C2}$ of the components (A3) and (C2), respectively, should satisfy the following formulas (III) and (IV):

$$80 \text{ wt. \%} \leq W_{A3}+W_{C2} \leq 100 \text{ wt. \%} \quad \text{(III)}$$

$$0.5 \leq W_{A3}/W_{C2} \leq 2.3 \quad \text{(IV)}$$

The weight percentage of each monomeric component is expressed in terms of a ratio of the weight of each monomeric component to the weight of the hindered amine compound. The weight of each monomeric component can be obtained by any one of conventional methods which are known as analyzing methods of polymers. Examples of quantitative analysis methods are the quantitative analysis with $^1$H-NMR, the quantitative analysis of the amount of a hindered amine component by neutralization titration, and the like. When it is difficult to quantitatively analyze a hindered amine compound, the weight percentage of the charged amount of each component may be used instead.

When the sum of the weight percentages of the components (A3) and (C2) is less than 80 wt. %, the stabilizingeffects cannot be attained with good balance after the processing of a resin composition. The sum of the weight percentages of the components (A3) and (C2) is preferably from 95 wt. % to 100 wt. %.

When the ratio of the weight percentage of the component (A3) to that of the component (C1) is less than 0.5, the hindered amine compound exerts low stabilizing effects prior to the processing of a resin composition, so that a large amount of the hindered amine compound should be compounded in a resin composition, which is unfavorable from the viewpoint of the costs. when this ratio exceeds 2.3, the stabilizing effects after the processing of a resin composition deteriorate, although the stabilizing effects prior to the processing are sufficient. This ratio is preferably in the range between 1.0 and 1.6.

R in the formula (5) is a substituted or unsubstituted alkyl group having 1 to 10 carbon atoms, preferably 1 to 4 carbon atoms, and more preferably methyl group.

$R^3$ in the formula (5) is a hydrogen atom or a methyl group, and a methyl group is preferable.

$R^4$ in the formula (5) is a hydrogen atom, a substituted or unsubstituted alkyl group having 1 to 10 carbon atoms, or an alkoxyl group having 1 to 10 carbon atoms. Among them, a hydrogen atom or an alkyl group having 1 to 4 carbon atoms is preferred from the viewpoint of stabilizing effects, and a hydrogen atom or a methyl group is more preferable.

$X^1$ in the formula (5) is a —O— group or a —NH— group, and a —O— group is preferable.

The polymerizable hindered amine monomeric compound (A3) is a single compound of the formula (5) or a mixture of two or more compounds of the formula (5), which may be the compounds of the formula (5) wherein each of $R^3$, $R^4$ and $X^1$ is the same or different. The most preferred combination of $R_3$, $R^4$ and $X^1$ is such that $R^3$ is a methyl group, $R^4$ is a hydrogen atom and $X^1$ is a —O— group.

Preferred examples of the polymerizable hindered amine monomeric compound (A3) include 2,2,6,6-tetramethyl-4-piperidyl methacrylate, 2,2,6,6-tetramethyl-4-piperidyl acrylate, 1,2,2,6,6-pentamethyl-4-piperidyl methacrylate, 1,2,2,6,6-pentamethyl-4-piperidyl acrylate, N-(2,2,6,6-tetramethyl-4-piperidyl) methacrylamide, N-(1,2,2,6,6-pentamethyl-4-piperidyl) methacrylamide, N-(2,2,6,6-tetramethyl-4-piperidyl) acrylamide, N-(1,2,2,6,6-pentamethyl-4-piperidyl) acrylamide, etc. Among them, 2,2,6,6-tetramethyl-4-piperidyl methacrylate, 2,2,6,6-tetramethyl-4-piperidyl acrylate, 1,2,2,6,6-pentamethyl-4-piperidyl methacrylate and 1,2,2,6,6-pentamethyl-4-piperidyl acrylate are more preferred. The most preferred compound is 2,2,6,6-tetramethyl-4-piperidyl methacrylate.

The component (A3) may be a mixture of two or more compounds as defined above with any composition. In particular, it is preferred to use 2,2,6,6-tetramethyl-4-piperidyl methacrylate alone.

$R^5$ in the formula (6) is a hydrogen atom or a methyl group, and a methyl group is preferable.

$R^6$ in the formula (6) is a cycloalkyl group having 5 to 10 carbon atoms or its derivative. When the number of carbon atoms in $R^6$ is too small, the effect exerted by each group is small. When the number of carbon atoms is too large, the number of groups decreases, and thus the effects exerted by the whole groups decreases so that the sufficient stabilizing effects after the processing of a resin composition cannot be attained.

A cycloalkyl group used herein means a group having at least one closed ring consisting of a plurality of carbon atoms which are covalentlybonded. Whenonecycloalkyl group hastwoormore rings, the rings may share some carbon atoms. In a cycloalkyl group, each ring has at least 3 carbon atoms, preferably 5 or 6 carbon atoms.

A cycloalkyl group may have at least one straight or branched alkyl group having 1 to 5 carbon atoms as a substituent. Although the number of the substituent alkyl groups on a cycloalkyl group is not limited, the total number of carbon atoms of the substituent alkyl groups is generally 5 to 10. Preferably, a cycloalkyl group consists of carbon and hydrogen atoms.

Furthermore, a cycloalkyl group has only covalent bonds, and neither a double bond nor a triple bond, from the viewpoint of the stabilizing effects. The bonding site of $R^6$ with $X^2$ may be either a carbon atom on the cycloalkyl group, or on an alkyl group which may be present as a substituent on the cycloalkyl group.

Specific examples of $R^6$ are the compounds of the following formulas (26) to (35):

(26)

(27)

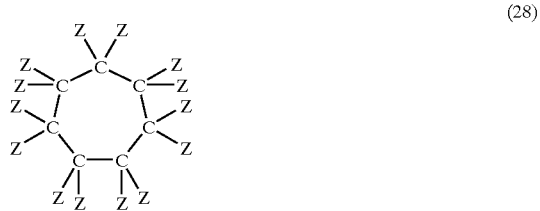

(28)

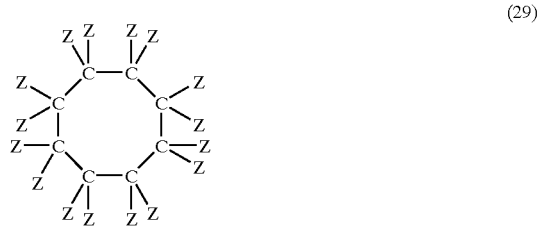

(29)

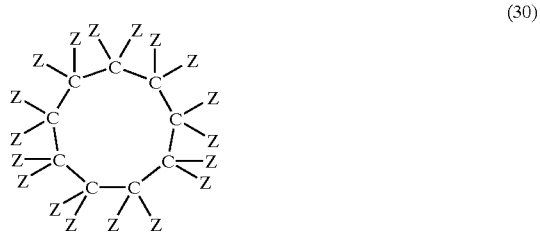

(30)

-continued

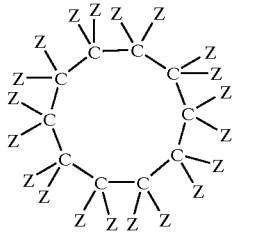
(31)

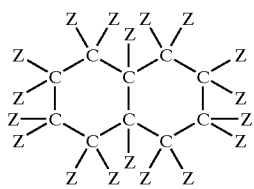
(32)

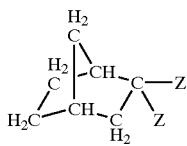
(33)

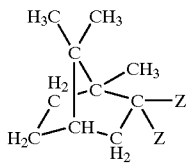
(34)

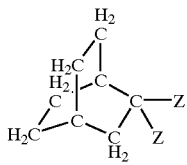
(35)

wherein Z is a hydrogen atom, a straight or branched alkyl group having 1 to 5 carbon atoms or a bonding site with $Y^1$, provided that the total number of carbon atoms in each formula does not exceed 10, and one of Z's is a bonding site with $Y^1$.

Preferable examples of $R^6$ include a cyclopentyl group, a cyclohexyl group, a cycloheptyl group, a cyclooctyl group, a cyclononyl group, a cyclodecyl group, a decahydronaphtyl group, a norbornyl group, a bornyl group, an isobornyl group, etc. Among them, a cyclohexyl group and an isobornyl group are more preferred.

$Y^1$ in the formula (6) is a —O— group or a —NH— group, and the —O— group is preferable.

The polymerizable monomeric compound (C2) is a single compound of the formula (6) or a mixture of two or more compounds of the formula (6), which may be the compounds of the formula (6) wherein each of $R^5$, $R^6$ and $Y^1$ is the same or different. The most preferred combination of $R^5$, $R^6$ and $Y^1$ is such that $R^5$ is a methyl group, $R^6$ is a cyclohexyl group and $Y^1$ is a —O— group.

Preferred examples of the polymerizable monomeric compound (C2) include cyclopentyl methacrylate, cyclohexyl methacrylate, cycloheptyl methacrylate, cyclooctyl methacrylate, cyclononyl methacrylate, cyclodecyl methacrylate, decahydronaphthyl methacrylate, norbornyl methacrylate, bornyl methacrylate, isobornyl methacrylate, cyclopentyl acrylate, cyclohexyl acrylate, cycloheptyl acrylate, cyclooctyl acrylate, cyclononyl acrylate, cyclode- cyl acrylate, decahydronaphtyl acrylate, norbornyl acrylate, bornyl acrylate, isobornyl acrylate, N-cyclopentyl methacrylamide, N-cyclohexyl methacrylamide, N- cycloheptyl methacrylamide, N-cyclooctyl methacrylamide, N-cyclononyl methacrylamide, N-cyclodecyl methacrylamide, N-decahydronaphtyl methacrylamide, N-norbornyl methacrylamide, N-bornyl methacrylamide, N-isobornyl methacrylamide, N-cyclopentyl methacrylamide, N-cyclohexyl acrylamide, N-cycloheptyl acrylamide, N-cyclooctyl acrylamide, norbornyl methacrylate, norbornyl acrylate, N-norbornylacrylamide, N-cyclononyl acrylamide, N-cyclodecyl acrylamide, N-decahydronaphthyl acrylamide, N-norbornyl acrylamide, N-bornyl acrylamide, N-isobornyl acrylamide, etc. Preferable examples of the polymerizable monomeric compound (C2) include cyclohexyl methacrylate, cyclohexyl acrylate, isobornyl methacrylate, isobornyl acrylate, etc. Among them, cyclohexyl methacrylate is more preferable.

In the hindered amine compound according to the third aspect of the present invention, the most preferred combination of the polymerizable hindered amine monomeric compound (A3) and the polymerizable monomer (C2) is the combination of 2,2,6,6-tetramethyl-4-piperidyl methacrylate and cyclohexyl methacrylate.

The hindered amine compound according to the fourth aspect of the present invention is a hindered amine compound obtained by copolymerizing at least one polymerizable hindered amine monomeric compound (A4) of the formula (7) and at least one polymerizable monomer (D1) of the formula (8). In addition, the weight percentages $W_{A4}$ and $W_{D1}$ of the components (A4) and (D1), respectively, satisfy the following formulas (V) and (VI):

$$80 \leq W_{A4} + W_{D1} \leq 100 \qquad (V)$$

$$0.3 \leq W_{A4}/W_{D1} \leq 2.3 \qquad (VI)$$

The weight percentage of each monomeric component is expressed in terms of a ratio of the weight of each monomeric component to the weight of the hindered amine compound. The weight of each monomeric component can be obtained by any one of conventional methods which are known as analyzing methods of polymers. Examples of quantitative analysis methods are the quantitative analysis with $^1$H-NMR, the quantitative analysis of the amount of a hindered amine component by neutralization titration, and the like. When it is difficult to quantitatively analyze a hindered amine compound, the weight percentage of the charged amount of each component may be used instead.

When the sum of the weight percentages of the components (A4) and (D1) is less than 80 wt. %, the stabilizing-effects cannot be attained with good balance after the processing of a resin composition. The sum of the weight percentages of the components (A4) and (D1) is preferably from 95 wt. % to 100 wt. %.

When the ratio of the weight percentage of the component (A4) to that of the component (D1) is less than 0.3, the hindered amine compound exerts low stabilizing effects prior to the processing of a resin composition, so that a large amount of the hindered amine compound should be compounded in a resin composition, which is unfavorable from the viewpoint of the costs. when this ratio exceeds 2.3, the stabilizing effects after the processing of a resin composition deteriorate, although the stabilizing effects prior to the processing are sufficient. This ratio is preferably in the range between 0.7 and 1.6.

R in the formula (7) is a substituted or unsubstituted alkyl group having 1 to 10 carbon atoms, preferably 1 to 4 carbon atoms, and more preferably methyl group.

$R^7$ in the formula (7) is a hydrogen atom or a methyl group, and a methyl group is preferable.

$R^8$ in the formula (7) is a hydrogen atom, a substituted or unsubstituted alkyl group having 1 to 10 carbon atoms, or an alkoxyl group having 1 to 10 carbon atoms. Among them, a hydrogen atom or an alkyl group having 1 to 4 carbon atoms is preferred from the viewpoint of stabilizing effects, and a hydrogen atom or a methyl group is more preferable.

$X^2$ in the formula (7) is a —O— group or a —NH— group, and a —O— group is preferable.

The polymerizable hindered amine monomeric compound (A4) is a single compound of the formula (7) or a mixture of two or more compounds of the formula (7), which may be the compounds of the formula (7) wherein each of $R^7$, $R^8$ and $X^2$ is the same or different. Preferably, each of $R^7$, $R^8$ and $X^2$ is the same. The most preferred combination of R7, $R^8$ and $X^2$ is such that $R^7$ is a methyl group, $R^8$ is a hydrogen atom and $X^2$ is a —O— group.

Preferred examples of the polymerizable hindered amine monomeric compound (A4) include 2,2,6, 6-tetramethyl-4-piperidyl methacrylate, 2,2,6,6-tetramethyl-4-piperidyl acrylate, 1,2,2,6,6-pentamethyl-4-piperidyl methacrylate, 1,2,2,6,6-pentamethyl-4-piperidyl acrylate, N-(2,2,6,6-tetramethyl-4-piperidyl) methacrylamide, N-(1,2,2,6,6-pentamethyl-4-piperidyl) methacrylamide, N-(2,2,6,6-tetramethyl-4-piperidyl) acrylamide, N-(1,2,2,6,6-pentamethyl-4-piperidyl) acrylamide, etc. Among them, 2,2, 6,6-tetramethyl-4-piperidyl methacrylate, 2,2,6,6-tetramethyl-4-piperidyl acrylate, 1,2,2,6,6-pentamethyl-4-piperidyl methacrylate and 1,2,2,6,6-pentamethyl-4-piperidyl acrylate are more preferred. The most preferred compound is 2,2,6,6-tetramethyl-4-piperidyl methacrylate.

The component (A4) may be a mixture of two or more compounds as defined above with any composition. In particular, it is preferred to use 2,2,6,6-tetramethyl-4-piperidyl methacrylate alone.

$R^9$ in the formula (8) is a hydrogen atom or a methyl group, and a methyl group is preferable.

$R^{10}$ in the formula (8) is a straight or branched alkyl group having 10 to 30 carbon atoms. When the number of carbon atoms in $R^{10}$ is too small, the effect exerted by each group is small. When the number of carbon atoms is too large, the number of groups decreases, and thus the effects exerted by the whole groups decreases so that the sufficient stabilizing effects after the processing of a resin composition cannot be attained.

Preferable examples of alkyl groups for $R^{10}$ include a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a docosyl group, a tetracosyl group, a hexacosyl group, an octacosyl group, a triacontyl group, an isostearyl group, etc. More preferable examples include a dodecyl group, a tetradecyl group, a hexadecyl group, an octadecyl group, etc.

$Y^2$ is a —O— group or a —NH— group, and a —O— group is preferable.

The polymerizable monomeric compound (D1) is a single compound of the formula (8) or a mixture of two or more compounds of the formula (8), which may be the compounds of the formula (8) wherein each of $R^9$, $R^{10}$ and $Y^2$ is the same or different. Preferably, each of $R^9$, $R^{10}$ and $Y^2$ is the same. The most preferred combination of $R^9$, $R^{10}$ and $Y^2$ is such that $R^9$ is a methyl group, $R^{10}$ is an octadecyl group and $Y^2$ is a —O— group.

Preferable examples of the polymerizable monomeric component (D1) include dodecyl methacrylate, tetradecyl methacrylate, hexadecyl methacrylate, octadecyl methacrylate, dodecyl acrylate, tetradecyl acrylate, hexadecyl acrylate, octadecyl acrylate, N-dodecyl methacrylamide, N-tetradecyl metharylamide, N-hexadecyl methacrylamide, N-octadecyl methacrylamide, N-dodecyl acrylamide, N-tetradecyl acrylamide, N-hexadecyl acrylamide, N-octadecyl acrylamide, etc.

In the hindered amine compound according to the fourth aspect of the present invention, the most preferred combination of the polymerizable hindered amine monomeric compound (A4) and the polymerizable monomer (D1) is the combination of 2,2,6,6-tetramethyl-4-piperidyl methacrylate and octadecyl methacrylate.

The hindered amine compounds according to the fifth and sixth aspects of the present invention are the copolymer of the compound of the formula (5) and the compound of the formula (6), and the copolymer of the compound of the formula (7) and the compound of the formula (8), respectively.

The hindered amine compounds according to the third, fourth, fifth and sixth aspects of the present invention can be synthesized from the above described compounds as the raw materials. It may be possible to copolymerize at least one of known polymerizable monomers which are not essential components of the hindered amine compounds of the present invention, insofar as the effects of the present invention are not impaired.

The polymerization reaction may be carried out by any known methods. A radical polymerization method is preferable, and a solution polymerization method, in which raw materials are reacted in a solvent in the presence of a radical polymerization initiator, is more preferable since the method is simple and the reaction can be easily controlled. Any solvent may be used, insofar as it does not react with radicals, and the polymerizable monomers and produced copolymers can be dissolved in it. Specific examples of such solvents include hydrocarbons (e.g. toluene, benzene, xylene, etc.), esters (e.g. ethyl acetate, butyl acetate, etc.), ketones (e.g. acetone, methyl ethyl ketone, etc.), alcohols (e.g. methanol, ethanol, isopropanol, n-butanol, etc.), N,N-dimethylformamide, N,N-dimethylacetamide, N-methylpyrrolidone, hexamethylphosphoneamide, etc.), ethers (e.g. diethyl ether, tetrahydrofuran, dioxane, ethylene glycol monomethyl ether, ethylene glycol monobutyl ether, etc.), and the like.

Any known polymerization initiator may be used in the present invention. In particular, azo compounds are preferable. Specific examples of azo compound include 2,2'-azobis(2-diaminopropane) dihydrochloride, 1,1'-azobis (cyclohexane-1-carbonitrile), 2,2'-azobis(2-methylbutyronitrile), 2,2'-azobis(isobutyronitrile), 2,2'-azobis(2,4-dimethylvaleronitrile), 2,2'-azobis(4-methoxy-2, 4-dimethylvaleronitrile), 4,4'-azobis(4-cianovaleric acid), dimethyl 2,2'-azobisisobutyrate, 2,2'-azobis[2-(2-imidazolin-2-yl)propane] dihydrochloride, 2,2'-azobis[2-(2-imidazolin-2-yl)propane] dihydrochloride dihydrate, 2,2'-azobis]2-(2-imidazolin-2-yl)propane], 2,2'-azobis{2-methyl-N-[1,1-bis(hydroxymethyl)-2-hydroxyethyl] propionamide}, 2,2'-azobis{2-methyl-N-[1,1-bis (hydroxymethyl)methyl]propionamide}, 2,2'-azobis[2-methyl-N-(2-hydroxyethyl)propionamide], 2,2'-azobisisobutylamide dihydrate, 2,2'-azobis[2-(hydroxymethyl)propionitrile], 2,2'-azobis[N-(2-propenyl)-2-methylpropionamide], 2,2'-azobis(2,4,4-trimethylpentane), etc.

The concentration of the polymerizable monomers at the charging is not limited, and is preferably from 20 to 70 wt %. A solvent may be supplemented, as the polymerization reaction proceeds.

The amount of the polymerization initiator added can be freely changed according to the intended degree of polymerization. The amount of the polymerization initiator is usually from 0.01 to 2 wt. % of the weight of the polymerizable monomers. The polymerization initiator as such or the solution of the polymerization initiator may be added to the polymerization system. The polymerization initiator may be added all at once, or portion by portion.

If necessary, any known chain transfer agent may be used.

The reaction temperature is not limited, and is preferably from 50 to 100° C.

The reaction time is not limited either, and is preferably from 1 to 24 hours.

The content of unreacted polymerizable monomers remained in the polymer composition is not limited, and is preferably not larger than 20 wt. % of the polymer weight. When the amount of the unreacted polymerizable monomers in the hindered amine compound is too large, they themselves deteriorate the compound and thus the stabilizing effects of the hindered amine compound may impaired. The obtained polymer may be used in the form of a solution, or it maybe purified by any known purification method such as reprecipitation, the removal of the solvent, column chromatography, etc., and then used.

R in the formula (9) is a substitutedorunsubstitutedalkyl group having 1 to 10 carbon atoms, preferably 1 to 4 carbon atoms, and methyl group is more preferable. $R^{11}$ and $R^{12}$ in the formula (9) are the same or different and each a hydrogen atom or methyl group, preferably each a methyl group. $R^{13}$ in the formula (9) is a hydrogen atom, a substituted or unsubstituted alkyl group having 1 to 10 carbon atoms, or an alkoxy group having 1 to 10 carbon atoms, preferably hydrogen atom or methyl group, and hydrogen atom is more preferable. X and Y in the formula (9) are the same or different and each a —O— group or a —NH— group, preferably each a —O— group. In formula (9), n/m is from 0.35 to 1.75, preferably from 0.70 to 1.70, and sum of n and m is from 2 to 10000, preferably from 5 to 1000.

R in the formula (10) is a substituted or unsubstituted alkyl group having 1 to 10 carbon atoms, preferably 1 to 4 carbon atoms, and methyl group is more preferable. $R^{14}$ and $R^{15}$ in the formula (10) are the same or different and each a hydrogen atom or methyl group, preferably each a methyl group. $R^{16}$ in the formula (10) is a hydrogen atom, a substituted or unsubstituted alkyl group having 1 to 10 carbon atoms, or an alkoxy group having 1 to 10 carbon atoms, preferably hydrogen atom or methyl group, and hydrogen atom is more preferable. $R^{17}$ in the formula (10) is a straight or branched alkyl group having 10 to 30 carbon atoms. Preferable example for $R^{17}$ include a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a docosyl group, a tetracosyl group, a hexacosyl group, anoctacosyl group, a triacontyl group, an isostearyl group, etc, and a dodecyl group, tetradecyl group, a hexadecyl group, and an octadecyl group are more preferable. X and Y in the formula (10) are the same or different and each a —O— group or a —NH— group, preferably each a —O— group. In formula (10), n/m is from 0.65 to 2.50, preferably from 1.30 to 2.30, and sum of n and m is from 2 to 10000, preferably from 5 to 1000.

The molecular weight of the hindered amine compound is not limited, and is preferably from 1,000 to 500,000. When the molecular weight is less than 1,000, the mobility of the compound in the resin increases so that the compound may bleed out. When the molecular weight exceeds 500,000, the compound may have adverse influences on the properties of the resin, and it may have less stabilizing effects than the compound having the smaller molecular weight. Preferably, the molecular weight of the hindered amine compound is from 2,000 to 200,000. The hindered amine compound having a suitable molecular weight can be used in accordance with applications and purposes.

The molecular weight of the hindered amine compound can be measured by any known method such as a gel permeation chromatographic method, a light scattering method, an osmotic pressure method, etc.

In the hindered amine compound of the present invention, at least a part of the hindered amino groups may form salts with at least one compound selected from the group consisting of organic carboxylic acids, carbon dioxide, phosphoric acid compounds, phosphate esters, phosphorous acid compounds and phosphite esters. It is possible to adjust the basicity or solubility of the hindered amine compound by forming the salts of at least a part of the hindered amine groups with the above compound(s) without deteriorating the inherent stabilizing function of the hindered amine compound.

Organic carboxylic acids are preferably those having 1 to 10 carbon atoms. In particular, saturated carboxylic acids are preferable. In addition, monocarboxylic acids are more preferable than polycarboxylic acids. Specific examples of organic carboxylic acids include formic acid, acetic acid, propionic acid, butyric acid, valeric acid, caproic acid, enanthic acid, caprylic acid, pelargonic acid, capric acid, acetoacetic acid, pyruvic acid, oxalic acid, malonic acid, succinic acid, glutaric acid, adipic acid, benzoic acid, naphthoacetic acid, phenylacetic acid, etc.

Phosphoric acid compounds include phosphoric acid and its salts with basic compounds such as amines, metal ions, etc., and phosphorous acid compounds include phoshorous acid and its salts with basic compounds such as amines, metal ions, etc.

Phosphate esters are preferably monoesters or diesters of phosphoric acid, while phosphate esters may be polymeric compounds a part of which has a monoester or diester structure of phosphoric acid. Phosphite esters are preferably monoesters or diesters of phosphorous acid, while phosphite esters may be polymeric compounds a part of which has a monoester or diester structure of phosphorous acid. The phosphate or phosphite esters may be partial salts with basic compounds such as amines, metal ions, etc.

The hindered amine compounds of the present invention can be used as stabilizers of known resins. Examples of such resins include polyurethane, polyamide, polyester, polyolefin, polystyrene, and mixtures or blends thereof.

The resin composition of the present invention contains a phosphite ester antioxidant and/or a phenol antioxidant.

A phosphite ester antioxidant may be any known compound, and a suitable compound is selected by taking into account its solubility in a solvent, compatibility with the resins such as polyurethane, and the like. Examples of phosphite ester antioxidants include tetrakis(2,4-di-tert.-butylphenyl) 4,4'-biphenylenephosphite, tris(nonylphenyl) phosphite, tris(2,4-di-tert.-butylphenyl) phosphite, distearylpentaerithritol diphosphite, di(2,4-di-tert.-butylphenyl) pentaerithritol diphosphite, di(2,6-di-tert.-butyl-4-methylphenyl)pentaerithritol diphosphite, triphenyl phosphite, diphenylisodecyl phosphite, phenyldiisodecyl phosphite, 4,4'-butylidene-bis(3-methyl-6-tert.-butylphenyl-ditridedyl) phosphite, cyclic neopentantetrayl (octadecylphosphite), tris(mono- and/or dinonylphenyl) phosphite, diisodecylpentaerithritol diphosphite, 2,2-methylenebis(4,6-di-tert.-butylphenyl)octyl phosphite, bis(tridecyl)pentaerithritol diphosphite, bis(nonylphenyl)-pentaerithritol diphosphite, hydrogenated bisphenol A-pentaerithritol phosphite polymer, hydrogenated bisphenol A phosphite polymer, tetraphenyltetra(tridecyl) pentaerithritol tetraphosphite, tetra(tridecyl)-4,4'-isopropylidenediphenyl diphosophite, tetraphenyldipropyleneglycol diphosphite, etc. Among them, hydrogeneated bisphenol A-pentaerithritol phosphite polymer and hydrogenated bisphenol A phosphite polymer are preferable. The phosphite ester antioxidant is compounded in polyurethane in an amount such that the degradation of polyurethane can be sufficiently suppressed in the practical application. Two or more phosphite ester antioxidants may be used. The amount of the phosphite ester antioxidant(s) is preferably from 0.1 to 2 wt. % of the weight of polyurethane.

A phenol antioxidant may be any known compound, and a suitable compound is selected by taking into account its solubility in a solvent, compatibility with the resin such as polyurethane, and the like. Examples of phenol antioxidants include pentaerithritol tetrakis [3-(3,5-di-tert.-butyl-4-hydroxyphenyl)propionate], octadecyl-3-(3,5-di-tert.-butyl-4-hydroxyphenyl) propionate, 1,1,3-tris(2-methyl-4-hydroxy-5-tert.-butylphenyl)butane, 1,3,5-tris(4-tert.-butyl-3-hydroxy-2,6-dimethyl)isocyanuric acid, 1,3,5-tris(4-sec.-butyl-3-hydroxy-2,6-dimethyl)isocyanuric acid, 1,3,5-tris(4-neopentyl-3-hydroxy-2,6-dimethyl)isocyanuric acid, 2,2'-methylenebis(4-methyl-6-tert.-butylphenol), 4,4'-butylidenebis(4-methyl-6-tert.-butylphenol), 1,3,5-trimethyl-2,4,6-tris(3,5-di-tert.-butyl-4-hydroxybenzyl) benzene, tris(3,5-di-tert.-butyl-4-hydroxybenzyl) isocyanurate, 3,9-bis{2-[3-(3-tert.-butyl-4-hydroxy-5-methylphenyl)propionyloxy)-1,1-dimethylethyl]-2,4,8,10-tetraoxaspiro[5.5]undecane, triethyleneglycol bis[3-(3-tert.-butyl-5-methyl-4-hydroxyphenyl)propionate], 1,6-hexanediol bis[3-(3,5-di-tert.-butyl-4-hydroxyphenyl) propionate], N,N'-hexamethylenebis(3,5-di-tert.-butyl-4-hydroxy-hydrocinnamide), diethyl 3,5-di-tert.-butyl-4-hydroxybenzylphosphonate, tris(3,5-di-tert.-butyl-4-hydroxybenzyl) isocyanurate, isooctyl 3-(3,5-di-tert.-butyl-4-hydroxyphenyl)propionate, N,N'-bis[3-(3,5-di-tert.-butyl-4-hydroxyphenyl)propionyl]hydrazine, a polycondensate of p-chloromethylstyrene and p-cresol, a polycondensate of p-chloromethylstyrene and divinylbenzene, a reaction product of isobutylene with a polycondensate of p-cresol and divinylbenzene, etc. Among them, 1,3,5-tris(4-tert.-butyl-3-hydroxy-2,6-dimethyl)isocyanuric acid, 1,3,5-tris(4-sec.-butyl-3-hydroxy-2,6-dimethyl)isocyanuric acid and 1,3,5-tris(4-neopentyl-3-hydroxy-2,6-dimethyl)isocyanuric acid are preferable, and 1,3,5-tris(4-tert.-butyl-3-hydroxy-2,6-dimethyl)isocyanuric acid is more preferable. The phenol antioxidant is compounded in polyurethane in an amount such that the degradation of polyurethane can be sufficiently suppressed in the practical application. Two or more phenol antioxidants may be used. The amount of the phenol antioxidant(s) is preferably from 0.1 to 2 wt. % of the weight of polyurethane.

A resin composition containing the hindered amine compound of the present invention can be shaped or molded by any known method, and processed by any known method.

The application of the resin composition is not limited, and the resin composition can be shaped in the form of fiber, film, sheet, molded article, foam, artificial leather, elastomer, paint, adhesive, non-woven fabric, and the like.

The resin composition containing the hindered amine compound of the present invention has excellent properties for the fiber application.

Examples of fibers include synthetic fibers such as polyurethane fiber, polyester fiber, polyamide fiber, acrylic fiber, acetate fiber, rayon fiber, polynosic fiber, cupra fiber, polyethylene fiber, polypropylene fiber, poly(vinirydene chloride) fiber, poly(vinyl chloride) fiber, etc. Inparticular, the hindered amine compound of the present invention is suitable for polyurethane resins and polyurethane fibers, and more suitable for polyurethane fibers.

Polyurethane used in the present invention may be any known polyurethane such as polyether polyurethane, polyester polyurethane, polycarbonate polyurethane, etc.

Such polyurethane can be obtained by reacting a polyisocyanate, a polymer diol, and optionally a low molecular weight polyfunctional active-hydrogen compound.

Examples of polyisocyanates include 4,4'-diphenylmethane diisocyanate, 1,4-phenylene diisocyanate, 2,4-tolylene diisocyanate, 2,6-tolylene diisocyanate, naphthalene diisocyanate, hexamethylene diisocyanate, 1,4-cyclohexane diisocyanate, 4,4'-dicyclohexylmethane diisocyanate, xylylene diisocyanate, and mixtures thereof. Among them, 4,4'-diphenylmethane diisocyanate is preferable.

A polymer diol is a substantially linear polymer having hydroxyl groups at both ends and a molecular weight of 600 to 7,000. Examples of polymer diols include polyether polyols (e.g. polytetramethylene ether glycol, polypropylene ether glycol, polyethylene ether glycol, polypentamethylene ether glycol, etc.), copolyether polyols having two or more alkylene groups having 1 to 6 carbon atoms (e.g. copoly(tetramethylene-neopentylene) ether diol, copoly(tetramethylene-2-methylbutylene) ether diol, copoly(tetramethylene-2,3-dimethylbutylene)ether diol, copoly(tetrametylene-2,2-dimethylbutylene) ether diol, etc.), polyester polyols prepared from at least one dibasic acid (e.g. adipic acid, sebacic acid, maleic acid, itaconic acid, azelaic acid, malonic acid, succinic acid, glutaric acid, suberic acid, dodecanedicarboxylic acid, β-methyladipic acid, hexahydroterephthalic acid, etc.) with at least one glycol (e.g. ethylene glycol, 1,2-propylene glycol, 1,4-butanediol, 1,6-hexanediol, neopentyl glycol, 1,4-dimethylolcyclohexane, etc.), polyetherester diol, polylactone diol, polycarbonate diol, and the like.

A low molecular weight polyfunctional active-hydrogen compound may be a compound having two or more active hydrogen atoms reactive with isocyanate groups (chain extender). Examples of chain extenders include polyamines (e.g. ethylenediamine, 1,2-diaminopropane, 1,3-diaminopropane, 1,4-diaminopropane, diethylenetriamine, triethylenetetramine, etc.), polyols (e.g. ethylene glycol, butanediol, etc.), polyhydrazide, polysemicarbazone, polyhydroxyamine, water, hydrazine, and mixtures thereof.

In addition to a chain extender, a compound having only one active hydrogen atom reactive with an isocyanate group may be used as a chain terminator. Examples of a compound having only one active hydrogen atom in a molecule include dialkylamines (e.g. diethylamine, dimethylamine, dibutylamine, diethanolamine, etc.), monoalkylamines (e.g. ethylamine, n-propylamine, isopropylamine, n-butylamine, tert.-butylamine, ethanolamine, etc.), monohydric alcohols (e.g. n-butanol, etc.), dehydrated condensates of diamine and ketones (e.g. a 1:1 reaction product of ethylenediamine and acetone), N,N-dimethylhydrazine, and mixtures thereof.

Polyurethane may be prepared by any conventional polymerization methods such as melt polymerization, solution polymerization, etc. A polymerization method may be a one-shot method in which all raw materials are mixed and reacted at once, or a prepolymer method in which a prepolymer is first prepared and then chain extended. A suitable amount of a reaction rate regulator such as an organic acid (e.g. acetic acid, p-toluenesulfonic acid, etc.) or carbon dioxide may be added at any step of the polymerization reaction. The reaction rate regulator is preferably added after the formation of the prepolymer and prior to the termination of a chain-extending reaction. The reaction rate regulator may be added together with a chain extender or a chain terminator.

The obtained polyurethane can be shaped by any conventional method and used in respective applications.

The hindered amine compound of the present invention may be compounded in a resin in any step, for example, up to a spinning step in the case of the production of fibers. The hindered amine compound of the present invention may be compounded in raw materials for polymerization, insofar as it has no influence on the polymerization reaction of the raw materials to produce a resin, or a resin from which fibers are produced. Alternatively, the hindered amine compound of the present invention may be compounded in a resin, or a resin from which fibers are produced, after the termination of the polymerization reaction, preferably after the termination of the polymerization reaction and prior to the shaping of the resin.

The hindered amine compound of the present invention may be used together with any conventional additives such as antioxidants (e.g. phenol antioxidants, phosphite ester antioxidants, thioether antioxidants, etc.), UV ray absorbers (e.g. benzotriazole UV ray absorbers, benzophenone UV ray absorbers, triazine UV ray absorbers, etc.), metal deactivators (e.g. dihydrazide derivative metal deactivators, oxalic acid derivative metal deactivators, etc.), anti-sticking agents (e.g. magnesium stearate, higher fatty acid amides, higher fatty acid esters, polyorganosilanes, polytetrafluoroethylene, etc.), inorganic fine particles (e.g. titanium dioxide, magnesium oxide, zinc oxide, hydrotalcite, barium sulfate, magnesium silicate, calcium silicate, etc.), flame retardants, antifungals, and the like.

When the hindered amine compound of the present invention is compounded in fibers, and a resin composition is melt spun, the hindered amine compound may be compounded in the raw material resin by melt kneading.

Among the other additives, the UV ray absorber is preferably compounded in a polyurethane resin composition, since it can significantly improve the light stability of the polyurethane resin composition. A suitable UV ray absorber may be selected from conventional UV ray absorbers such as benzotriazole UV ray absorbers, benzophenone UV ray absorbers, triazine UV ray absorbers, oxalinide UV ray absorbers, and the like depending on the purpose. Among them, benzotriazole UV ray absorbers and triazine UV ray absorbers are preferable.

Specific examples of benzotriazole UV ray absorbers include 2-(2-hydroxy-5-methylphenyl)benzotriazole, 2-(2-hydroxy-3,5-di-tert.-butylphenyl)-5-chlorobenzotriazole, 2-(2-hydroxy-3-tert.-butyl-5-methylphenyl)-5-chlorobenzotriazole, 2-(2-hydroxy-3,5-di-tert.-amylphenyl) benzotriazole, 2-(2-hydroxy-3,5-di-tert.-butylphenyl) benzotriazole, 2-(2-hydroxy-5-methyl-3-(3,4,5,6-tetrahydrophthalimidoylomethyl)phenyl]benzotriazole, 2-(2-hydroxy-5-tert.-butylphenyl)benzotriazole, 2-(2-hydroxy-5-tert.-octylphenyl)benzotriazole, 2-[2-hydroxy-3,5-bis(α,α-dimethylbenzyl)phenyl]-2H-benzotriazole, 2,2-methylenebis[4-(1,1,3,3-tetramethylbutyl)-6-(2H-benzotriazole-2-yl)phenol], a condensate of methyl-3-[3-tert.-butyl-5-(2H-benzotriazol-2-yl) -4-hydroxyphenyl] propionate and polyethylene glycol, etc.

Examples of triazine UV ray absorbers include 2-(4,6-diphenyl-1,3,5-triazin-2-yl)-5-[(hexyl)oxy]-phenol, 2,4-di(2',4'-dimethylphenyl)-6-(2"-hydroxy-4"-n-octyloxyphenyl)-1,3,5-triazine, etc.

Among those UV ray absorbers, 2-(2-hydroxy-3,5-di-tert.-amyl)benzotriazole and 2-[2-hydroxy-3,5-bis(α,α-dimethylbenzyl)phenyl]-2H-benzotriazole are preferable.

The above UV ray absorbers may be used independently or in admixture of two or more.

The amount of the UV ray absorber is preferably from 0.1 to 2.0 wt. % of the weight of polyurethane.

The polyurethane fiber of the present invention can be prepared by spinning the polyurethane resin composition of the present invention. When the resin composition is spun by a wet or dry spinning method, the hindered amine compound of the present invention can be compounded in a spinning dope by mixing the hindered amine compound as such or in the form of a solution with the spinning dope. Spinning machines or spinning conditions are not limited, and any conventional spinning method can be selected according to the composition of the resin composition, applications, purposes, the properties of fibers, etc. The hindered amine compound of the present invention is suitable as a stabilizer of fibers, in particular, polyurethane fibers. Among the polyurethane fibers, those produced by wet or dry spinning of a polyurethane solution is significantly stabilized with the hindered amine compound of the present invention.

The hindered amine compound of the present invention is compounded in a resin composition in an amount such that the stabilizing function is well exerted in accordance with the kinds and applications of resins or fibers. Although not limited, the amount of the hindered amine compound of the present invention is preferably from 0.05 to 10 wt. % of the weight of the resin or fiber. In particular, the amount of the hindered amine compound of the present invention is from 0.5 to 5 wt. % in the case of the polyurethane resin composition or the polyurethane fiber.

A polyester fiber, which is used in combination with a polyurethane fiber in a stretch fabric or knit of the present invention, may be any conventionally used polyester fiber. A typical example of such a polyester fiber is a polyethylene terephthalate fiber.

A polyamide fiber, which is used in combination with a polyurethane fiber in a stretch fabric or knit of the present invention, may be any conventionally used polyamide fiber such as fibers of Nylon 6, Nylon 66 and Nylon 46, their cation-dyeable modified fibers, as well as polyamide-polyester composite fibers. Fibers having any fineness and cross section can be used.

A cellulose fiber, which is used in combination with a polyurethane fiber in a stretch fabric or knit of the present invention, may be any conventionally used cellulose fiber such as cotton fibers, rayon fibers, their blended fibers with polyester fibers, and composite fibers with Nylon/polyester filaments. Fibers having any fineness can be used.

A fiber, which is used in combination with a polyurethane fiber in a stretch fabric or knit of the present invention, may be any non-stretch fiber, for example, fur such as wool, cashmere, alpaca, etc., silk, acrylic fiber, promix fiber, and the like.

A polyurethane fiber used in a stretch fabric or knit of the present invention is usually in the form of a bare yarn, or a composite elastic yarn such as a single-covering yarn, a double-covering yarn, a core spun yarn or a ply yarn.

The stretch fabric or knit of the present invention comprises the polyurethane elastic yarn, and a non-stretch yarn of a polyester fiber, a polyamide fiber, a cellulose fiber, and the like.

A stretch fabric may be a plain weave, a twill weave, a satin weave, etc., which uses the polyurethane yarn as a warp and/or a weft. A stretch knit may be a circular knit such as a plain stitch, an interlock stitch, a rib stitch, a purl stitch, and their modificatins, or a warp knit such as a tricot, a Russel cord, etc.

The texture of knitting can be a half stitch, a reverse half stitch, a double demby stitch, a double atlas stitch, et. in the case of a tricot, or a power net, a half power net, a satin net, a triconet, etc. in the case of a Russel cord.

EXAMPLES

The present invention will be illustrated by the following Examples, which do not limit the scope of the present invention in any way. In the Examples, "parts" and "%" are "parts by weight" and "% by weight", respectively, unless otherwise indicated.

Model Treating Method for Dyeing

A tubular knit material for evaluation is treated with hot water at 95° C. for 1 minute, and then in an air at 190° C. for 60 seconds. Thereafter, the tubular knit material (about 7 g) is treated with the about 20 times weight of a model dyeing liquid in a sealed container at 98° C. for 30 minutes. The model dyeing liquid is a solution of a dyeing auxiliary (NEWPON TS 100 available from NICCA CHEMICAL Co., Ltd.) (0.5 g), acetic acid (0.5 g) and sodium acetate (0.25 g) dissolved in pure water (1 liter). After that, the tubular knit material is washed with water, dried and treated in an air at 180° C. for 60 seconds.

Discoloring Test with $NO_x$

A tubular knit material for evaluation (about 1 g) is contained in a sealed container and exposed to $NO_2$ for 1.5 hours by continuously flowing an air containing 200 ppm of $NO_2$, which is generated with PERMEATOR PD-1-B (manufacture by GASTECH Co., Ltd.), in the container at a flow rate of 500 ml/min. After the exposure to $NO_2$, the knit material is well washed with a buffered urea solution, which is defined in JIS L 0855, and then pure water, and dried in a nitrogen stream for 24 hours. After that, eight plies of the knit material are laminated and the "b" value of the laminate according to the Hunter's Lab color system is measured with a color meter (TC 1500MC-88 manufactured by TOKYO DENSHOKU Co., Ltd.). The larger "b" value means the larger discoloration.

A degree of discoloration (Δb) is calculated according to the following equation (X):

Δb=("b" value after the treatment with $NO_2$) −("b" value prior to the treatment with $NO_2$)   (X)

The smaller Δb means the less discoloration and the better stabilizing effects.

Embrittling Test with Chlorine

The tenacity (g) of a polyurethane fiber, which is obtained by unknitting a tubular knit sample prior to the treatment with chlorine, is measured.

A tubular knit sample is continuously treated at 25° C. for 10 hours with an aqueous chlorine solution having an effective chlorine concentration of 3 ppm and pH of 7.5, which is prepared from a commercially available aqueous solution of sodium hypochlorite. Then, the treated sample is washed with pure water and dried in a nitrogen stream for 24 hours.

The tenacity (g) of the polyurethane fiber, which is obtained by unknitting the tubular knit sample after the treatment with chlorine, is measured, and the retention of tenacity (%) is calculated from the tenacity prior to the treatment with chlorine and that after the treatment with chlorine.

Synthesis Example 1

(Synthesis of a Hindered Amine Compound)

In a 500 cc side-arm flask equipped with a thermometer, a stirrer, a nitrogen inlet tube and a reflux condenser, 2,2,6,6-tetramethyl-4-piperidyl methacrylate (ADK STAB LA-87 manufactured by ASAHI DENKA KOGYO KK) (60 parts), cyclohexyl methacrylate (40 parts) and N,N-dimethylacetamide (213 parts) were charged and stirred to dissolve them. The flask was heated on an oil bath to 60° C. while stirring and bubbling nitrogen gas through the solution. After the temperature of the solution reached 60° C., 2,2'-azobis (isobutyronitrile) (AIBN) (0.8 part) was added, and the contents in the flask were reacted while maintaining 60° C. and stirring. After 5 hours from the first addition of AIBN, AIBN (0.2 part) was added, and the reaction was continued at 60° C. for 15 hours. Then, the reaction mixture was cooled to room temperature to terminate the reaction. Thus, the solution of a hindered amine compound was obtained.

The viscosity of the reaction mixture was 15 poises when it was measured at 30° C. with an E-type viscometer using a rotor with an apex angle of 3 degrees and a diameter of 14 mm.

The amount of the unreacted polymerizable monomers in the reaction mixture was measured with gas chromatography. It was found that 4 wt. % of the charged polymerizable monomers remained unreacted.

The number average molecular weight of the product was 2,700 in terms of a molecular weight of polystyrene, when it was measured with gel permeation chlomatography using tetrahydrofuran as a solvent and a refractometer as a detector.

A $^1$H-NMR spectrum of the obtained hindered amine compound was measured using a mixed solvent of DMSO-d6 and CDCl (1:1 by volume) at 50° C. The protons of the methine carbons on the pyperidyl group and those of the methine carbons on the cyclohexyl group were detected at 5.0 ppm and 4.6 ppm, respectively, and the integrated ratio was 52:48. Since this integrated ratio is assumed to correspond to the molar ratio of the units obtained from 2,2,6,6-tetramethyl-4-piperidyl methacrylate to those obtained from cyclohexyl methacrylate, the weight percentages of these two monomeric units were calculated to be 60 wt. % and 40 wt. %, respectively, which are consistent with the percentages calculated from the charged amounts.

Synthesis Example 2

A hindered amine compound was prepared in the same manner as that of Synthesis Example 1 except that 65 parts of 2,2,6,6-tetramethyl-4-piperidyl methacrylate and 35 parts of cyclohexyl methacrylate were used as polymerizable monomers.

Synthesis Example 3

A hindered amine compound was prepared in the same manner as that of Synthesis Example 1 except that 45 parts of 2,2,6,6-tetramethyl-4-piperidyl methacrylate and 55 parts of cyclohexyl methacrylate were used as polymerizable monomers.

Synthesis Example 4

A hindered amine compound was prepared in the same manner as that of Synthesis Example 1 except that 40 parts of 2,2,6,6-tetramethyl-4-piperidyl methacrylate, 45 parts of cyclohexyl methacrylate and 15 parts of hydroxyethyl methacrylate were used as polymerizable monomers.

Synthesis Example 5

A hindered amine compound was prepared in the same manner as that of Synthesis Example 1 except that 60 parts of 2,2,6,6-tetramethyl-4-piperidyl methacrylate and 40 parts of stearyl methacrylate were used as polymerizable monomers.

Synthesis Example 6

A hindered amine compound was prepared in the same manner as that of Synthesis Example 1. Then, 5.3 parts of acetic acid was added to the prepared hindered amine compound and well mixed to obtain a hindered amine compound.

Comparative Synthesis Example 1

A hindered amine compound was prepared in the same manner as that of Synthesis Example 1 except that 80 parts of 2,2,6,6-tetramethyl-4-piperidyl methacrylate and 20 parts of cyclohexyl methacrylate were used as polymerizable monomers.

Comparative Synthesis Example 2

A hindered amine compound was prepared in the same manner as that of Synthesis Example 1 except that 20 parts of 2,2,6,6-tetramethyl-4-piperidyl methacrylate and 80 parts of cyclohexyl methacrylate were used as polymerizable monomers.

Comparative Synthesis Example 3

A hindered amine compound was prepared in the same manner as that of Synthesis Example 1 except that 50 parts of 2,2,6,6-tetramethyl-4-piperidyl methacrylate and 50 parts of methyl methacrylate were used as polymerizable monomers.

Comparative Synthesis Example 4

A hindered amine compound was prepared in the same manner as that of Synthesis Example 1 except that 40 parts of 2,2,6,6-tetramethyl-4-piperidyl methacrylate, 20 parts of cyclohexyl methacrylate and 30 parts of hydroxyethyl methacrylate were used as polymerizable monomers.

Solubility of a Hindered Amine Compound in an Acidic Solution

The solution of the hindered amine compound obtained in each of Synthesis Examples 1–5 and Comparative Synthesis Examples 1–4 was dropwise added into pure water to precipitate the compound. The precipitate was recovered by filtration, and dried under reduced pressure at 80° C. for 12 hours. The solubility of the obtained hindered amine compound in an acidic solution was measured by the above-described method. Methanol was used as a solvent for titration.

Example 1

Preparation of Polyurethane Solution

Polytetramethylene ether glycol having a number average molecular weight of 1,800 (175.37 parts) and 4,4'-diphenylmethane diisocyanate (38.92 parts) were reacted at 80° C. for 3 hours under a nitrogen stream to obtain a prepolymer having isocyanate groups at both chain ends.

The prepolymer was cooled to 40° C., and N,N-dimethylacetamide (308.36 parts) was added to dissolve the prepolymer, followed by cooling to 10° C.

The solution of ethylenediamine (3.58 parts) and diethylamine (0.46 part) in N,N-dimethylacetamide (146.86 parts) was added all at once to the prepolymer solution which was rapidly stirred to complete the reaction. The viscosity of this solution was 2,000 poises at 30° C.

To this solution, the hindered amine compound obtained in Sythesis Example 1 (13.42 parts), 1,3,5-tris(4-tert.-butyl-3-hydroxy-2,6-dimethylbenzylisosyanurate) as an antioxidant (CYANOX 1790 available from NIPPON CYANAMIDE) (2.15 parts), 2-[(2-hydroxy-3,5-di-tert.-amyl)phenyl]benzotriazole as a UV ray absorber (KEMISORB 74 available from KEMIPRO KASEI Co., Ltd.) (1.08 parts) and magnesium stearate as an anti-sticking agent (0.69 part) were added and mixed to obtain a polyurethane solution.

[Preparation of polyurethane fiber and preparation of sample for evaluation]

After deaeration, the polyurethane solution was extruded through a spinning nozzle having 4 orifices with a diameter of 0.3 mm into a spinning barrel in which a hot air at 230° C. was flown, and the spun fiber was taken up at 500 m/min. while applying 5 wt. % of an oil to the fiber to obtain a polyurethane fiber of 44 decitex.

Using a circular knitting machine with one feeder (manufactured by KOIKE SEISAKUSHO), a cylindrical knit material was produced, which consisted of the polyurethane fiber and had 108 courses/inch and 178 wales/inch. This knit material was used as a sample for evaluation.

A part of the knit material sample was subjected to the model treating method for dyeing as an example of secondary processing. The untreated and treated tubular knit material samples were subjected to various tests to evaluate the stabilizing effects.

Examples 2–5

A tubular knit material was prepared and evaluated in the same manners as those of Example 1 except that the hindered amine compound solution prepared in each of Synthesis Examples 2–5 was used in place of the hindered amine compound solution prepared in Synthesis Example 1.

Examples 2–5 used the hindered amine compound prepared in Synthesis Examples 2–5, respectively.

Example 6

A tubular knit material was prepared and evaluated in the same manners as those of Example 1 except that the hindered amine compound solution prepared in Synthesis Example 6 was used in place of the hindered amine compound solution prepared in Synthesis Example 1.

Example 7

A tubular knit material was prepared and evaluated in the same manners as those of Example 1 except that hydrogenated bisphenol A-pentaerithritol phosphite polymer (JPH-3800 available from JOHOKU CHEMICAL CO., LTD.) was used in place of 1,3,5-tris(4-tert.-butyl-3-hydroxy-2,6-dimethylbenzylisosyanurate).

Comparative Examples 1–4

A tubular knit material was prepared and evaluated in the same manners as those of Example 1 except that the hindered amine compound solution prepared in each of Comparative Synthesis Examples 1–4 was used in place of the hindered amine compound solution prepared in Synthesis Example 1.

Comparative Examples 1–4 used the hindered amine compound prepared in Comparative Synthesis Examples 1–4, respectively.

Comparative Example 5

A tubular knit material was prepared and evaluated in the same manners as those of Example 1 except that 4.30 parts of a condensate of 1,2,3,4-butanetetracarboxylic acid, 2,2,6,6-tetramethyl-4-piperidinol and β,β,β',β'-tetramethyl-3,9-(2,4,8,10-tetraoxaspiro[5.5]undecane)diethanol (ADK STAB LA-68LD manufactured by ASAHI DENKA KOGYO KK) was used in place of 13.42 parts of the hindered amine compound solution prepared in Synthesis Example 1.

Comparative Example 6

A tubular knit material was prepared and evaluated in the same manners as those of Example 1 except that 4.30 parts of a condensate of 1,2,3,4-butanetetracarboxylic acid and 2,2,6,6-tetramethyl-4-piperidinol (ADK STAB LA-57 manufactured by ASAHI DENKA KOGYO KK) was used in place of 13.42 parts of the hindered amine compound solution prepared in Synthesis Example 1.

Comparative Example 7

A tubular knit material was prepared and evaluated in the same manners as those of Example 1 except that 4.30 parts of a polyaddition product of 4-ethyl-2,6-dimethyl-azaheptanediol and methylene-bis(4-cyclohexylisocyanate), which is a conventional anti-discoloration agent, was used in place of a hindered amine compound solution.

For the polyurethane fiber tubular knit materials obtained in Examples and Comparative Examples, the structural parameters obtained from the chemical structures, and the results of various tests before and after the model treating method for dyeing are summarized in Table 1.

The polyurethane fibers containing the hindered amine compounds of the present invention had less degrees of discoloration with $NO_x$ after the model treating method for dyeing and thus better stabilized after processing than the polyurethane fibers containing the hindered amine compounds outside the scope of the present invention.

Furthermore, the polyurethane fibers containing the hindered amine compounds of the present invention had less degrees of discoloration with $NO_x$ after the model treating method for dyeing and suffered less deterioration of tenacity caused by the chlorinated water than the polyurethane fiber containing the tertiary amine compound which is a conventional stabilizer.

TABLE 1

|  | No. of (A1) groups in 1 kg of hindered amine compound (mole/kg) | Solubility in acidic solution (eq/liter) | $W_{A2} + W_{C1}$ | $W_{A2}/W_{C1}$ | $W_{A3} + W_{C2}$ | $W_{A3}/W_{C2}$ | $W_{A4} + W_{D1}$ | $W_{A4}/W_{D1}$ | Discoloration with $NO_x$ (b value) Before/after model treating method for dyeing | Embrittleness with chlorinate water (tenacity retention: %) |
|---|---|---|---|---|---|---|---|---|---|---|
| Ex. 1 | 2.7 | $0.5 \times 10^{-3}$ | 57 | 1.9 | 100 | 1.5 | 60 | — | 12/14 | 105/81 |
| Ex. 2 | 2.9 | $2.3 \times 10^{-3}$ | 57 | 2.4 | 100 | 1.9 | 65 | — | 11/16 | 99/83 |
| Ex. 3 | 2.0 | $0.3 \times 10^{-3}$ | 55 | 1.0 | 100 | 1.2 | 45 | — | 13/15 | 95/79 |
| Ex. 4 | 1.8 | $0.2 \times 10^{-3}$ | 47 | 1.1 | 85 | 1.1 | 40 | — | 13/16 | 101/82 |
| Ex. 5 | 2.7 | $4.5 \times 10^{-3}$ | 37 | — | 100 | — | 100 | 1.5 | 12/18 | 97/84 |
| Ex. 6 | 2.6 | $0.7 \times 10^{-3}$ | 54 | 1.9 | 95 | 1.5 | 60 | — | 11/13 | 93/80 |
| Ex. 7 | 2.7 | $0.5 \times 10^{-3}$ | 57 | 1.9 | 100 | 1.5 | 60 | — | 8/10 | 80/80 |
| C. Ex. 1 | 3.6 | $7.6 \times 10^{-3}$ | 60 | 5.0 | 100 | 4.0 | 80 | — | 10/24 | 95/77 |
| C. Ex. 2 | 0.9 | $0.1 \times 10^{-3}$ | 52 | 0.3 | 100 | 0.3 | 20 | — | 18/20 | 94/76 |
| c. Ex. 3 | 2.2 | $8.9 \times 10^{-3}$ | 31 | — | 50 | — | 50 | — | 13/25 | 103/78 |
| C. Ex. 4 | 1.8 | $7.6 \times 10^{-3}$ | 35 | 2.5 | 60 | 2.0 | 40 | — | 14/24 | 96/82 |
| C. Ex. 5 | 3.5 | $7.2 \times 10^{-3}$ | 49 | — | 0 | — | 0 | — | 9/26 | 101/85 |
| C. Ex. 6 | 6.0 | $9.3 \times 10^{-3}$ | 50 | — | 0 | — | 0 | — | 8/25 | 98/87 |
| C. Ex. 7 | — | $0.3 \times 10^{-3}$ | 0 | — | 0 | — | 0 | — | 18/21 | 21/20 |

Example 8

Preparation of Polyurethane Solution

Polytetramethylene ether glycol having a number average molecular weight of 1,800 (175.37 parts) and 4,4'-diphenylmethane diisocyanate (38.92 parts) were reacted at 80° C. for 3 hours under a nitrogen stream to obtain a prepolymer having isocyanate groups at both chain ends.

The prepolymer was cooled to 40° C., and N,N-dimethylacetamide (308.36 parts) was added to dissolve the prepolymer, followed by cooling to 10° C.

The solution of ethylenediamine (3.58 parts) and diethylamine (0.46 part) in N,N-dimethylacetamide (146.86 parts)

was added all at once to the prepolymer solution which was stirred at a high speed to complete the reaction. The viscosity of this solution was 2,000 poises at 30° C.

To this solution, the hindered amine compound obtained in Sythesis Example 1 (13.42 parts), 1,3,5-tris(4-tert.-butyl-3-hydroxy-2,6-dimethylbenzylisosyanurate) as an antioxidant (CYANOX 1790 available from NIPPON CYANAMIDE) (2.15 parts), 2-[(2-hydroxy-3,5-di-tert.-amyl)phenyl]benzotriazole as a UV ray absorber (KEMISORB 74 available from KEMIPRO KASEI Co., Ltd.) (1.08 parts), hydrogenated bisphenol A-pentaerithritol phosphite polymer as a phosphite ester antioxidant (JPH-3800 available from JOHOKU CHEMICAL CO., LTD.) (2.15 parts) and magnesium stearate as an anti-sticking agent (0.69 part) were added and mixed to obtain a polyurethane solution.

[Preparation of Polyurethane Fiber and Preparation of Sample for Evaluation]

After deaeration, the polyurethane solution was extruded through a spinning nozzle having 4 orifices with a diameter of 0.3 mm into a spinning barrel in which a hot air at 230° C. was flown, and the spun fiber was taken up at 500 m/min. while applying 5 wt. % of an oil to the fiber to obtain a polyurethane fiber of 44 decitex.

Using a circular knitting machine with one feeder (manufactured by KOIKE SEISAKUSHO), a tubular knit material was produced, which consisted of the polyurethane fiber and had 108 courses/inch and 178 wales/inch. This knit material was used as a sample for evaluation.

Example 9

A sample for evaluation was produced in the same manner as that of Example 8 except that a polycondensate of p-chloromethylstyrene and p-cresol (2.15 parts) was used as a phenol antioxidant.

Example 10

A sample for evaluation was produced in the same manner as that of Example 8 except that di(2,4-di-tert.-butylphenyl) pentaerithritol diphosphite (2.15 parts) was used as a phosphite ester antioxidant.

Example 11

A sample for evaluation was produced in the same manner as that of Example 8 except that a polycondensate of p-chloromethylstyrene and p-cresol (2.15 parts) was used as a phenol antioxidant, and di(2,4-di-tert.-butylphenyl) pentaerithritol diphosphite (2.15 parts) was used as a phosphite ester antioxidant.

Example 12

A sample for evaluation was produced in the same manner as that of Example 8 except that the hindered amine compound obtained in Synthesis Example 6 was used as a hindered amine compound.

Comparative Example 8

A sample for evaluation was produced in the same manner as that of Example 8 except that the hindered amine compound obtained in Comparative Synthesis Example 1 was used as a hindered amine compound.

Comparative Example 9

A sample for evaluation was produced in the same manner as that of Example 8 except that the hindered amine compound obtained in Comparative Synthesis Example 2 was used as a hindered amine compound.

Comparative Example 10

A sample for evaluation was produced in the same manner as that of Example 8 except that 4.30 parts of a condensate of 1,2,3,4-butanetetracarboxylic acid, 2,2,6,6-tetramethyl-4-piperidinol and $\beta,\beta,\beta',\beta'$-tetramethyl-3,9-(2,4,8,10-tetraoxaspiro[5.5]undecane)diethanol (ADK STAB LA-68LD manufactured by ASAHI DENKA KOGYO KK) was used as a hindered amine compound.

Comparative Example 11

A sample for evaluation was produced in the same manner as that of Example 8 except that 4.30 parts of bis(2,2,6,6-tetramethyl-4-piperidyl) sebacate (TINUVIN770DF available from Ciba Specialty Chemicals holding Inc.) was used as a hindered amine compound.

Comparative Example 12

A sample for evaluation was produced in the same manner as that of Example 8 except that 4.30 parts of the reaction product of 4-ethyl-2,6-dimethyl-4-azaheptanediol and methylene-bis(cyclohexylisocyanate) (having molecular weight of about 4,000), which isa conventional anti-discoloration agent, was used in place of a hindered amine compound solution.

Comparative Example 13

A sample for evaluation was produced in the same manner as that of Example 8 except that neither a hindered amine compound nor a phosphite ester antioxidant was used.

For the polyurethane fiber tubular knit materials obtained in Examples 8–12 and Comparative Examples 8–13, the results of the discoloration test with $NO_x$ before and after the model treating method for dyeing are summarized in Table 2.

The polyurethane fibers containing the hindered amine compounds of the present invention were less discolored with $NO_x$ and the stabilizing effects were maintained after the model treating method for dyeing. Some of the polyurethane fibers containing the hindered amine compounds outside the scope of the present invention exerted less stabilizing effects before and after dyeing, or others lost the stabilizing effects after dyeing even though they had the good stabilizing effects prior to dyeing.

When a conventional anti-discoloration agent was used in place of the hindered amine compound, the stabilizing effects were less lost, but the level of the stabilizing effects with the conventional anti-discoloration agent were inferior to those achieved with the hindered amine compounds of the present invention.

Accordingly, the polyurethane resin compositions and fibers of the present invention have good anti-$NO_x$ discoloration properties and maintain the stabilizing properties even after post-processing such as dyeing.

TABLE 2

| | | | | | | Hindered amine compound | | | | | | Discoloration with NOx (b value) | |
|---|---|---|---|---|---|---|---|---|---|---|---|---|---|
| | Phenol anti-oxidant | Phosphite ester anti-oxidant | Compound | No. of (A1) group in 1 kg (mole/kg) | Solubility in acidic solution (eq/liter) | $W_{A2} + W_{C1}$ | $W_{A2}/W_{C1}$ | $W_{A3} + W_{C2}$ | $W_{A3}/W_{C2}$ | n/m | | Before model treating method for dyeing | After model treating method for dyeing |
| Ex. 8 | a-1 | b-1 | c-1 | 2.7 | $0.5 \times 10^{-3}$ | 57 | 1.9 | 100 | 1.5 | 1.13 | | 5.1 | 7.2 |
| Ex. 9 | a-2 | b-1 | c-1 | 2.7 | $0.5 \times 10^{-3}$ | 57 | 1.9 | 100 | 1.5 | 1.13 | | 6.2 | 8.7 |
| Ex. 10 | a-1 | b-2 | c-1 | 2.7 | $0.5 \times 10^{-3}$ | 57 | 1.9 | 100 | 1.5 | 1.13 | | 6.9 | 9.3 |
| Ex. 11 | a-2 | b-2 | c-1 | 2.7 | $0.5 \times 10^{-3}$ | 57 | 1.9 | 100 | 1.5 | 1.13 | | 7.1 | 9.1 |
| Ex. 12 | a-1 | b-1 | c-2 | 2.7 | $0.7 \times 10^{-3}$ | 57 | 1.9 | 100 | 1.5 | 1.13 | | 5.3 | 7.8 |
| C. Ex. 8 | a-1 | b-1 | c-3 | 3.6 | $7.6 \times 10^{-3}$ | 60 | 5.0 | 100 | 4.0 | 3.00 | | 4.6 | 16.1 |
| C. Ex. 9 | a-1 | b-1 | c-4 | 0.9 | $0.1 \times 10^{-3}$ | 52 | 0.3 | 100 | 0.3 | 0.19 | | 13.2 | 14.9 |
| C. Ex. 10 | a-1 | b-1 | c-5 | 3.5 | $7.2 \times 10^{-3}$ | 49 | — | 0 | — | — | | 4.3 | 23.1 |
| C. Ex. 11 | a-1 | b-1 | c-6 | 4.2 | $6.5 \times 10^{-3}$ | 58 | — | — | — | — | | 10.2 | 22.9 |
| C. Ex. 12 | a-1 | b-1 | (d-1) | — | $0.3 \times 10^{-3}$ | — | — | — | — | — | | 12.0 | 14.7 |
| C. Ex. 13 | a-1 | — | — | — | — | — | — | — | — | — | | 22.6 | 25.0 |

Notes:
a-1: 1,3,5-Tris(4-tert.-butyl-3-hydroxy-2,6-dimethyl)isocyanuric acid (a phenol antioxidant)
a-2: A polycondensate of p-chloromethylstyrene and p-cresol (a phenol antioxidant)
b-1: Hydrogenated bisphaneol A-pentaerithritol phosphiate polymer (a phosphite ester antioxidant)
b-2: Di(2,4-di-tert.-butylphenyl) pentaerithritol diphosphite (a phosphite ester antioxidant)
c-1: A copolymer of 2,2,6,6-tetramethyl-4-piperidyl methacrylate and cyclohexyl methacrylate (Molar ratio (n/m) = 1.13) (Synthesis Example 1)
c-2: An acetate salt of a copolymer of 2,2,6,6-tetramethyl-4-piperidyl methacrylate and cyclohexyl methacrylate (Molar ratio (n/m) = 1.13) (Synthesis Example 6)
c-3: A copolymer of 2,2,6,6-tetramethyl-4-piperidyl methacrylate and cyclohexyl methacrylate (Molar ratio (n/m) = 3.00) (Comparative Synthesis Example 1, the present invention)
c-4: A copolymer of 2,2,6,6-tetramethyl-4-piperidyl methacrylate and cyclohexyl methacrylate (Molar ratio (n/m) = 0.19 (Comparative Synthesis Example 2, the present invention)
c-5: A condensate of 1,2,3,4-butanetetracarboxylic acid, 2,2,6,6-tetramethyl-4-piperidinol and β, β, β', β'-tetramethyl-3,9-(2,4,8,10-tetraoxaspiro[5.5]undecane)diethanol (a known hindered amine compound)
c-6: Bis(2,2,6,6-tetramethyl-4-piperidyl) sebacate (a known hindered amine compound)
d-1: A reaction product of 4-ethyl-2,6-diethyl-4-azaheptanediol and methylene-bis(cyclohexylisocyanate) (a known aliphatic amine derivative)

Synthesis Example 7
Synthesis of a Hindered Amine Compound

In a 500 cc side-arm flask equipped with a thermometer, a stirrer, a nitrogen inlet tube and a reflux condenser, 2,2,6,6-tetramethyl-4-piperidyl methacrylate (ADK STAB LA-87 manufactured by ASAHI DENKA KOGYO KK) (60 parts), octadecyl methacrylate (40 parts) and N,N-dimethylacetamide (213 parts) were charged and stirred to dissolve them. The flask was heated on an oil bath to 60° C. while stirring and bubbling nitrogen gas through the solution. After the temperature of the solution reached 60° C., 2,2'-azobis(isobutyronitrile) (AIBN) (0.8 part) was added, and the contents in the flask were reacted under a nitrogen stream while maintaining 60° C. and stirring. After 5 hours from the first addition of AIBN, AIBN (0.2 part) was supplemented, and the reaction was continued at 60° C. for 15 hours while stirring. Then, the reaction mixture was cooled to room temperature to terminate the reaction. Thus, the solution of a hindered amine compound was obtained.

The viscosity of the reaction mixture was 12 poises when it was measured 30° C. with an E-type viscometer using a rotor with an apex angle of 3 degrees and a diameter of 14 mm.

The amount of the monomers remained in the reaction mixture was measured with gas chromatography. It was found that 4 wt. % of the monomers based on the weight of the polymer (except the solvent) remained.

The number average molecular weight of the product was 2,900 in terms of a molecular weight of polystyrene, when it was measured with gel permeation chromatography using tetrahydrofuran as a solvent. The n/m calculated from the charged amounts was 2.27.

Synthesis Example 8

A hindered amine compound was prepared in the same manner as that of Synthesis Example 7. Then, 5.3 parts of acetic acid was added to the prepared hindered amine compound and well mixed to obtain a hindered amine compound.

Comparative Synthesis Example 5

A hindered amine compound was prepared in the same manner as that of Synthesis Example 7 except that the amounts of 2,2,6,6-tetramethyl-4-piperidyl methacrylate and octadecyl methacrylate were changed to 80 parts and 20 parts, respectively. The n/m calculated from the charged amounts was 6.05.

Comparative Synthesis Example 6

A hindered amine compound was prepared in the same manner as that of Synthesis Example 7 except that the amounts of 2,2,6,6-tetramethyl-4-piperidyl methacrylate and octadecyl methacrylate were changed to 20 parts and 80 parts, respectively. The n/m calculated from the charged amounts was 0.38.

Example 13

Preparation of Polyurethane Solution

Polytetramethylene ether glycol having a number average molecular weight of 1,800 (175.37 parts) and 4,4'-diphenylmethane diisocyanate (38.92 parts) were reacted at 80° C. for 3 hours under a nitrogen stream to obtain a prepolymer having isocyanate groups at both chain ends.

The prepolymer was cooled to 40° C., and N,N-dimethylacetamide (308.36 parts) was added to dissolve the prepolymer, followed by cooling to 10° C.

The solution of ethylenediamine (3.58 parts) and diethylamine (0.46 part) in N,N-dimethylacetamide (146.86 parts)

was added all at once to the prepolymer solution which was stirred at a high speed to complete the reaction. The viscosity of this solution was 2,000 poises at 30° C.

To this solution, the hindered amine compound obtained in Sythesis Example 7 (13.42 parts), 1,3,5-tris(4-tert.-butyl-3-hydroxy-2,6-dimethylbenzylisosyanurate) as an antioxidant (CYANOX 1790 available from NIPPON CYANAMIDE) (2.15 parts), 2-[(2-hydroxy-3,5-di-tert.-amyl)phenyl]benzotriazole as a UV ray absorber (KEMISORB 74 available from KEMIPRO KASEI Co., Ltd.) (1.08 parts), hydrogenated bisphenol A-pentaerithritol phosphite polymer as a phosphite ester antioxidant (JPH-3800 available from JOHOKU CHEMICAL CO., LTD.) (2.15 parts) and magnesium stearate as an anti-sticking agent (0.69 part) were added and mixed to obtain a polyurethane solution.

Preparation of Polyurethane Fiber and Preparation of Sample for Evaluation

After deaeration, the polyurethane solution was extruded through a spinning nozzle having 4 orifices with a diameter of 0.3 mm into a spinning barrel in which a hot air at 230° C. was flown, and the spun fiber was taken up at 500 m/min. while applying 5 wt. % of an oil to the fiber to obtain a polyurethane fiber of 40 denier.

Using a circular knitting machine with one feeder (manufactured by KOIKE SEISAKUSHO), a tubular knit material was produced, which consisted of the polyurethane fiber and had 108 courses/inch and 178 wales/inch. This knit material was used as a sample for evaluation.

Example 14

A sample for evaluation was produced in the same manner as that of Example 13 except that a polycondensate of p-chloromethylstyrene and p-cresol (2.15 parts) was used as a phenol antioxidant.

Example 15

A sample for evaluation was produced in the same manner as that of Example 13 except that di(2,4-di-tert.-butylphenyl) pentaerithritol diphosphite (2.15 parts) was used as a phosphite ester antioxidant.

Example 16

A sample for evaluation was produced in the same manner as that of Example 13 except that a polycondensate of p-chloromethylstyrene and p-cresol (2.15 parts) was used as a phenol antioxidant, and di(2,4-di-tert.-butylphenyl) pentaerithritol diphosphite (2.15 parts) was used as a phosphite ester antioxidant.

Example 17

A sample for evaluation was produced in the same manner as that of Example 13 except that the hindered amine compound obtained in Synthesis Example 8 was used as a hindered amine compound.

Comparative Example 14

A sample for evaluation was produced in the same manner as that of Example 13 except that the hindered amine compound obtained in Comparative Synthesis Example 5 was used as a hindered amine compound.

Comparative Example 15

A sample for evaluation was produced in the same manner as that of Example 13 except that the hindered amine compound obtained in Comparative Synthesis Example 6 was used as a hindered amine compound.

Comparative Example 16

A sample for evaluation was produced in the same manner as that of Example 13 except that 4.30 parts of a condensate of 1,2,3,4-butanetetracarboxylic acid, 2,2,6,6-tetramethyl-4-piperidinol and β,β,β',β'-tetramethyl-3,9-(2,4,8,10-tetraoxaspiro[5.5]undecane)diethanol (ADK STAB LA-68LD manufactured by ASAHI DENKA KOGYO KK) was used as a hindered amine compound.

Comparative Example 17

A sample for evaluation was produced in the same manner as that of Example 13 except that 4.30 parts of bis(2,2,6,6-tetramethyl-4-piperidyl) sebacate (TINUVIN 770DF available from Ciba Specialty Chemicals holding Inc.) was used as a hindered amine compound.

Comparative Example 18

A sample for evaluation was produced in the same manner as that of Example 13 except that 4.30 parts of the reaction product of 4-ethyl-2,6-dimethyl-4-azaheptanediol and methylene-bis(cyclohexylisocyanate) (having molecular weight of about 4,000), which is a conventional anti-discoloration agent, was used in place of a hindered amine compound solution.

Comparative Example 19

A sample for evaluation was produced in the same manner as that of Example 13 except that neither a hindered amine compound nor a phosphite ester antioxidant was used.

For the polyurethane fiber cylindrical knit materials obtained in Examples 13–17 and Comparative Examples 14–19, the results of the discoloration test with $NO_x$ before and after the model treating method for dyeing are summarized in Table 3.

The polyurethane fibers containing the hindered amine compounds of the present invention were less discolored with $NO_x$ and the stabilizing effects were maintained after the model treating method for dyeing. Some of the polyurethane fibers containing the hindered amine compounds outside the scope of the present invention exerted less stabilizing effects before and after dyeing, or others lost the stabilizing effects after dyeing even though they had the good stabilizing effects prior to dyeing.

When a conventional anti-discoloration agent was used in place of the hindered amine compound, the stabilizing effects were less lost, but the level of the stabilizing effects with the conventional anti-discoloration agent were inferior to those achieved with the hindered amine compounds of the present invention.

Accordingly, the polyurethane resin compositions and fibers of the present invention have good anti-$NO_x$ discoloration properties and maintain the stabilizing properties even after post-processing such as dyeing.

TABLE 3

| | Phenol antioxidant | Phospite ester antioxidant | Hindered amine compound | Discoloration with NOx (b value) Before model treating method for dyeing | Discoloration with NOx (b value) After model treating method for dyeing |
|---|---|---|---|---|---|
| Ex. 13 | a-1 | b-1 | c-7 | 5.3 | 8.5 |
| Ex. 14 | a-2 | b-1 | c-7 | 5.9 | 9.3 |
| Ex. 15 | a-1 | b-2 | c-7 | 6.2 | 9.9 |
| Ex. 16 | a-2 | b-2 | c-7 | 7.5 | 9.8 |
| Ex. 17 | a-1 | b-1 | c-8 | 5.9 | 8.9 |
| C. Ex. 14 | a-1 | b-1 | c-9 | 4.9 | 22.5 |
| C. Ex. 15 | a-1 | b-1 | c-10 | 12.8 | 15.6 |
| C. Ex. 16 | a-1 | b-1 | c-5 | 4.3 | 23.1 |
| C. Ex. 17 | a-1 | b-1 | c-6 | 10.2 | 22.9 |
| C. Ex. 18 | a-1 | b-1 | (d-1) | 12.0 | 14.7 |
| C. Ex. 19 | a-1 | — | — | 22.6 | 25.0 |

Notes:
a-1: 1,3,5-Tris(4-tert.-butyl-3-hydroxy-2,6-dimethyl)isocyanuric acid (a phenol antioxidant)
a-2: A polycondensate of p-chloromethylstyrene and p-cresol (a phenol antioxidant)
b-1: Hydrogenated bisphaneol A-pentaerithritol phosphiate polymer (a phosphite ester antioxidant)
b-2: Di(2,4-di-tert.-butylphenyl) pentaerithritol diphosphite (a phosphite ester antioxidant)
c-5: A condensate of 1,2,3,4-butanetetracarboxylic acid, 2,2,6,6-tetramethyl-4-piperidinol and β, β, β', β'-tetramethyl-3,9-(2,4,8,10-tetraoxaspiro[5.5]undecane)diethanol (a known hindered amine compound)
c-6: Bis(2,2,6,6-tetramethyl-4-piperidyl) sebacate (a known hindered amine compound)
c-7: A copolymer of (2,2,6,6-tetramethyl-4-piperidyl) methacrylate and octadecyl methacrylate (Molar ratio (n/m) = 2.27) (Synthesis Example 7)
c-8: An acetate salt of a copolymer of (2,2,6,6-tetramethyl-4-piperidyl) methacrylate and octadecyl methacrylate (Molar ratio (n/m) = 2.27) (Synthesis Example 8)
c-9: A copolymer of (2,2,6,6-tetramethyl-4-piperidyl) methacrylate and octadecyl methacrylate (Molar ratio (n/m) = 6.00) (Comparative Synthesis Example 5)
c-10: A copolymer of (2,2,6,6-tetramethyl-4-piperidyl) methacrylate and octadecyl methacrylate (Molar ratio (n/m) = 0.38) (Comparative Synthesis Example 6)
d-1: A reaction product of 4-ethyl-2,6-diethyl-4-azaheptanediol and methylene-bis(cyclohexylisocyanate) (a known aliphatic amine derivative)

[Production Example of Polyurethane Fiber for Stretch Fabric and Knit]

Polytetramethylene ether glycol having a number average molecular weight of 1,800 (175.37 parts) and 4,4'-diphenylmethane diisocyanate (38.92 parts) were reacted at 80° C. for 3 hours under a nitrogen stream to obtain a prepolymer having isocyanate groups at both chain ends.

The prepolymer was cooled to 40° C., and N,N-dimethylacetamide (308.36 parts) was added to dissolve the prepolymer, followed by cooling to 10° C.

The solution of ethylenediamine (3.58 parts) and diethylamine (0.46 part) in N,N-dimethylacetamide (146.86 parts) was added all at once to the prepolymer solution which was stirred at a high speed to complete the reaction. The viscosity of this solution was 2,000 poises at 300° C.

To this solution, the hindered amine compound obtained in Sythesis Example 1 (13.42 parts), 1,3,5-tris(4-tert.-butyl-3-hydroxy-2,6-dimethylbenzylisosyanurate) as an antioxidant (CYANOX 1790 available from NIPPON CYANAMIDE) (2.15 parts), 2-[(2-hydroxy-3,5-di-tert.-amyl)phenyl]benzotriazole as a UV ray absorber (KEMISORB 74 available from KEMIPRO KASEI Co., Ltd.) (1.08 parts), hydrogenated bisphenol A-pentaerithritol phosphite ester polymer as a phosphite ester antioxidant (JPH-3800 available from JOHOKU CHEMICAL CO., LTD.) (2.15 parts) and magnesium stearate as an anti-sticking agent (0.69 part) were added and mixed to obtain a polyurethane solution.

After deaeration, the polyurethane solution was extruded through a spinning nozzle into a spinning barrel in which a hot air at 230° C. was flown, to obtain a polyurethane elastic fiber (dry spinning).

[Comparative Production Example of Polyurethane Fiber for Stretch Fabric and Knit]

A polyurethane elastic fiber was produced in the same dry spinning method as that of the above Production Example except that the hindered amine prepared in Comparative Synthesis Example 1 was used in place of the hindered amine prepared in Synthesis Example 1.

Example 18

Using a Russel knitting machine (RSE-4N with a 130 inch width and 28 gauges manufactured by Karl Mayer), a cloth having a six courses-power net structure was knitted from the combination of a 310 decitex yarn of the polyurethane fiber produced in the above Production Example, and a 55 decitex-17 filament yarn of Nylon This cloth was refined and relaxed in a bath containing 1 g/liter of an anionic surfactant (MARPON T available from MATSUMOTO YUSHI-SEIYAKU CO., LTD.) at 80° C. for 90 seconds, and then dipped in warm water at 75° C. After the water content of the cloth was adjusted with a mangle to 30%, the cloth was heat set with a pin tenter at 190° C. for 30 seconds.

Thereafter, using a jet dyeing machine (Circular NX), the heat set cloth was dyed with a fluorescent white dye (Kayaphar WN available from NIPPON KAYAKU Co., Ltd.) (1% owf) and a levelling agent (Newbon TS available from NICCA CHEMICAL Co., Ltd.) (1% owf) in the presence of 0.5 g/liter of acetic acid and 0.15 g/liter of ammonium acetate at a bath ratio of 1:30 by heating the both from 40° C. to 90° C. over 40 minutes, and dyeing the cloth at 90° C. for 20 minutes. Then, the cloth was washed with warm water at 50° C. for 10 minutes twice, and finish set with a pin tenter at 160° C. for 30 seconds. Thus, the cloth having a warp density of 60 courses per inch and a weft density of 40 wales per inch, which was dyed with the fluorescent white dye, was obtained.

Before and after dyeing, the cloth was subjected to the above-described $NO_x$-discoloration test, and the "b" values before and after the treatment with $NO_x$ were measured. The results are shown in Table 4.

Example 19

Using a tricot knitting machine (HKS2 with a 180 inch width and 28 gauges manufactured by Karl Mayer), a two-way tricot cloth having a half structure was knitted from the combination of a 44 decitex yarn of the polyurethane fiber produced in the above Production Example, and a 55 decitex-12 filament yarn of Nylon 6 (triloval cross-section bright yarn).

This cloth was dyed with a fluorescent white dyestuff by the same method as that of Example 18. Thus, the cloth having a warp density of 100 courses per inch and a weft density of 60 wales per inch was obtained.

Before and after dyeing, the cloth was subjected to the above-described $NO_x$-discoloration test, and the "b" values before and after the treatment with $NO_x$ were measured. The results are shown in Table 4.

Example 20

Using a single circular knitting machine (XL-3FA with a 38 inch diameter and 28 gauges manufactured by FUKU- HARA SEIKI Co., Ltd.), a cloth having a bare in plain stitch was knitted from the combination of a 44 decitex yarn of the polyurethane fiber produced in the above Production Example, and a 165 decitex-48 filament yarn of polyester.

This cloth was dyed with a fluorescent white dyestuff by the same method as that of Example 18. Thus, the cloth having a warp density of 65 courses per inch and a weft density of 42 wales per inch was obtained.

Before and after dyeing, the cloth was subjected to the above-described $NO_x$-discoloration test, and the "b" values before and after the treatment with $NO_x$ were measured. The results are shown in Table 4.

Comparative Examples 20–22

A cloth was produced and dyed by the same methods as those of each of Examples 18–20 except that the polyurethane fiber which was produced in the above Comparative Production Example. Before and after dyeing, the cloth was subjected to the above-described $NO_x$-discoloration test, and the "b" values before and after the treatment with $NO_x$ were measured. The results are shown in Table 4.

As can be seen from the results in Table 4, the Δb values in Examples 18–20 are smaller than those in Comparative Examples 20–22. This means that the knit cloth of the present invention suffers less discoloration with $NO_x$ after dyeing.

TABLE 4

| Sample | Kind of cloth | Knit structure | Degree of discoloration (Δb) | |
| --- | --- | --- | --- | --- |
| | | | Before dyeing | After dyeing |
| Ex. 18 | Russel | Power net | 0.9 | 1.1 |
| C. Ex. 20 | Russel | Power net | 1.0 | 2.3 |
| Ex. 19 | Tricot | Half | 0.5 | 0.7 |
| C. Ex. 21 | Tricot | Half | 0.5 | 1.8 |
| Ex. 20 | Circular knit | Bare grey sheeting | 0.6 | 0.8 |
| C. Ex. 22 | Circular knit | Bare grey sheeting | 0.6 | 1.9 |

What is claimed is:
1. A hindered amine compound obtained by copolymerizing at least one polymerizable hindered amine monomeric compound (A3) of the formula (5):

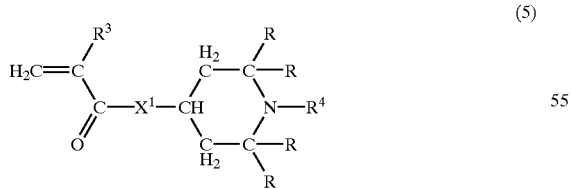

(5)

in which R is a straight or branched alkyl group having 1 to 10 carbon atoms, $R^3$ is a hydrogen atom or methyl group, $R^4$ is a hydrogen atom, a straight or branched alkyl group having 1 to 10 carbon atoms, or an alkoxy group having 1 to 10 carbon atoms, and $X^1$ is a —O— group or a —NH— group, and at least one polymerizable monomer (C2) of the formula (6):

(6)

in which $R^5$ is a hydrogen atom or a methyl group, $R^6$ is a cycloalkyl group having 5 to 10 carbon atoms, and $Y^1$ is a —O— group or a —NH— group, wherein the weight percentages $W_{A3}$ and $W_{C2}$ of the components (A3) and (C2), respectively, satisfy the following formulas (III) and (IV):

$$80 \leq W_{A3} + W_{C2} \leq 100 \tag{III}$$

$$0.5 \leq W_{A3}/W_{C2} \leq 2.3 \tag{IV}$$

2. A hindered amine compound obtained by copolymerizing at least one polymnerizable hindered amine monomeric compound (A4) of the formula (7):

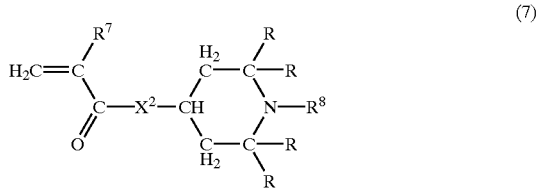

(7)

in which R is a straight or branched alkyl group having 1 to 10 carbon atoms, $R^7$ is a hydrogen atom or methyl group, $R^8$ is a hydrogen atom, a straight or branched alkyl group having 1 to 10 carbon atoms, or an alkoxy group having 1 to 10 carbon atoms, and $X^2$ is a —O— group or a —NH— group, and at least one polymerizable monomer (D1) of the formula (8):

(8)

in which $R^9$ is a hydrogen atom or a methyl group, $R^{10}$ is a straight or branched alkyl group having 10 to 30 carbon atoms, and $Y^2$ is a —O— group or a —NH— group, wherein the weight percentages $W_{A4}$ and $W_{D1}$ of the components (A4) and (D1), respectively, satisfy the following formulas (V) and (V1):

$$80 \leq W_{A4} + W_{D1} \leq 100 \tag{V}$$

$$0.5 \leq W_{A4}/W_{D1} \leq 2.3 \tag{VI}$$

3. A hindered amine compound of the formula (9):

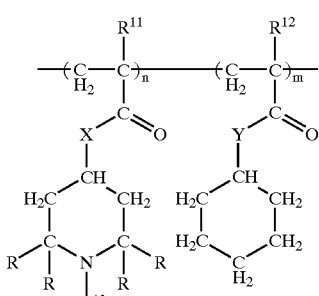

(9)

in which R is a straight or branched alkyl group having 1 to 10 carbon atoms, $R^{11}$ and $R^{12}$ are the same or different and each a hydrogen atom or a methy group, $R^{13}$ is a hydrogen atom, a straight or branched alkyl group having 1 to 10 carbon atoms, or an alkoxy group having 1 to 10 atoms, X and Y are the same or different and each a —O— group or a —NH— group, and n and m are positive integers satisfying the formula: $0.35 \leq n/m \leq 1.75$, and the sum of n and m is from 2 to 10000.

4. A hindered amine compound of the formula (10):

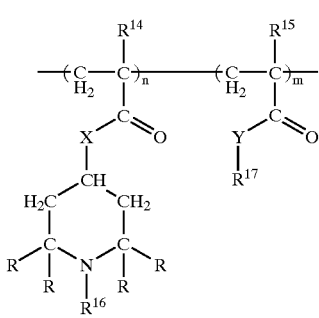

(10)

in which R is a straight or branched alkyl group having 1 to 10 carbon atoms, $R^{14}$ and $R^{15}$ are the same or different and each a hydrogen atom or a methyl group, $R^{16}$ is a hydrogen atom, a straight or branched alkyl group having 1 to 10 carbon atoms, or an alkoxy group having 1 to 10 atoms, $R^{17}$ is a straight or branched alkyl group having 10 to 30 carbon atoms, X and Y are the same or different and each a —O— group or a —NH— group, and n and m are positive integers satisfying the formula: $0.65 \leq n/m \leq 2.50$, and the sum of n and m is from 2 to 10000.

5. The hindered amine compound according to claim 1,2,3, or 4, wherein at least a part of the hindered amine groups of said hindered amine compound form salts with at least one compound selected from the group consisting of organic carboxylic acids, carbon dioxide, phosphoric acid, phosphate esters, phosphorous acid and phosphite esters.

6. A resin composition comprising a hindered amine compound according to claim 1,2,3, or 4.

7. A resin composition comprising a hindered amine compound according to claim 1,2,3, or 4, further comprising a phosphate ester antioxidant.

8. The resin composition according to claim 6 further comprising a phosphate ester antioxidant and wherein said resin is polyurethane.

9. A resin composition comprising polyurethane, a phenol antioxidant, a phosphate ester antioxidant, and the hindered amine compound according to claim 1,2,3, or 4.

10. The resin composition according to claim 9, wherein said phosphite ester antioxidant is a hydrogenated bisphenol A-pentaerythritol phosphite polymer which has the chemical structure of the formula (11):

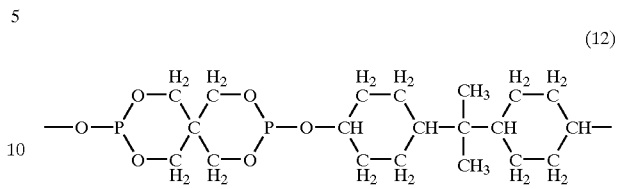

(12)

11. The resin composition according to claim 9, wherein said phenol antioxidant is a phenol compound of the formula (12):

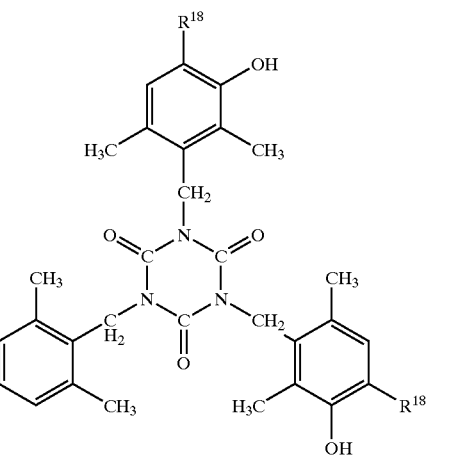

(12)

wherein $R^{18}$ is a tert.-butyl group, a sec-butyl group or a neopentyl group.

12. The resin composition according to claim 9, wherein the amount of the phenol antioxidant is from 0.1 to 2 wt. %, the amount of the phosphate ester is from 0.1 to 2 wt. %, and the amount of the hindered amine compound is from 0.5 to 5 wt. %, based on the weight of polyurethane.

13. A polyurethane fiber prepared from the polyurethane resin composition according to claim 8.

14. A method for the preparation of a polyurethane fiber comprising the step of spinning resin composition according to claim 8.

15. A stretch fabric or knit comprising a non-stretch fiber and the polyurethane fiber according to claim 13.

16. The stretch fabric or knit according to claim 15, wherein said non-stretch fiber is at least one fiber selected from the group consisting of a polyester fiber, a polyamide fiber and a cellulose fiber.

17. The stretch fabric or knit according to claim 15, wherein said polyurethane fiber is a bare fiber or a composite fiber.

18. A resin composition comprising a hindered amine compound according to claim 5.

19. The resin composition according to claim 18, further comprising a phosphite ester antioxidant.

20. The resin composition according to claim 18, wherein said resin is polyurethane.

21. The resin composition according to claim 19, wherein said resin is polyurethane.

22. A resin composition comprising polyurethane, a phenol antioxidant, a phosphite ester antioxidant, and the hindered amine compound according to claim 5.

23. The resin composition according to claim 10, wherein said phenol antioxidant is a phenol compound of the formula (12):

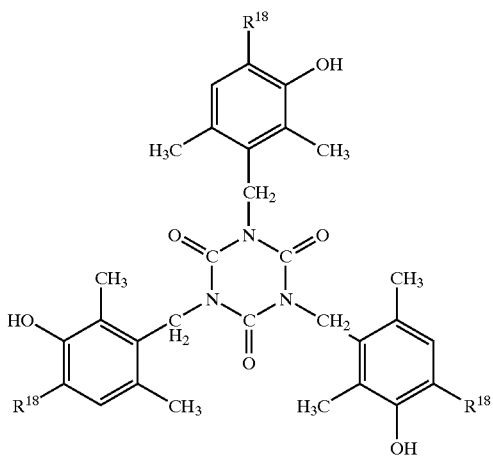

wherein $R^{18}$ is a tert-butyl group, a sec-butyl group or a neopentyl group.

24. The resin composition according to claim 22, wherein said phenol antioxidant is a phenol compound of the formula (12):

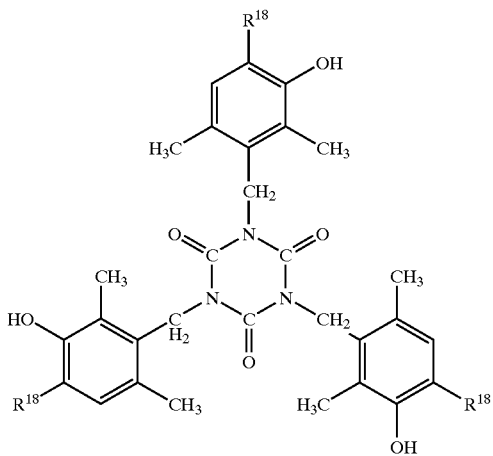

wherein $R^{18}$ is a tert-butyl group, a sec-butyl group or a neopentyl group.

25. The resin composition according to claim 10, wherein the amount of the phenol antioxidant is from 0.1 to 2 weight %, the amount of the phosphite ester is from 0.1 to 2 weight %, and the amount of the hindered amine compound is from 0.5 to 5 weight %, based on the weight of polyurethane.

26. The resin composition according to claim 11, wherein the amount of the phenol antioxidant is from 0.1 to 2 weight %, the amount of the phosphite ester is from 0.1 to 2 weight %, and the amount of the hindered amine compound is from 0.5 to 5 weight %, based on the weight of polyurethane.

27. A polyurethane fiber prepared from the polyurethane resin composition according to claim 9.

28. A polyurethane fiber prepared from the polyurethane resin composition according to claim 10.

29. A polyurethane fiber prepared from the polyurethane resin composition according to claim 11.

30. A polyurethane fiber prepared from the polyurethane resin composition according to claim 12.

31. A polyurethane fiber prepared from the polyurethane resin composition according to claim 20.

32. A polyurethane fiber prepared from the polyurethane resin composition according to claim 21.

33. A polyurethane fiber prepared from the polyurethane resin composition according to claim 22.

34. A polyurethane fiber prepared from the polyurethane resin composition according to claim 23.

35. A polyurethane fiber prepared from the polyurethane resin composition according to claim 24.

36. A polyurethane fiber prepared from the polyurethane resin composition according to claim 25.

37. A polyurethane fiber prepared from the polyurethane resin composition according to claim 26.

* * * * *

UNITED STATES PATENT AND TRADEMARK OFFICE
CERTIFICATE OF CORRECTION

PATENT NO. : 6,486,238 B1
DATED : November 26, 2002
INVENTOR(S) : Kitamura et al.

It is certified that error appears in the above-identified patent and that said Letters Patent is hereby corrected as shown below:

Title page,
Item [57], ABSTRACT,
Line 1, change "thesolubility" to -- the solubility --.

Column 3,
Line 23, change "awide varietyof" to -- a wide variety of --

Column 5,
Line 30, change "$5.0 \times 10_{31\ 3}$" to -- $5.0 \times 10^{-3}$ --

Column 9,
Line 36, change "substitutedor" to -- substituted or --

Column 14,
Line 13, change "atleastone organicgroup" to -- at least one organic group --
Line 13, change "inonemolecule" to -- in one molecule --
Line 14, change "totalweight" to -- total weight --
Line 21, change "whichisunfavorablefromtheviewpointof" to
-- which is unfavorable from the view point of --
Line 25, change "stabilizingeffectsprior" to -- stabilizing effects prior --
Line 25, change "the processingrelativelyincrease" to -- the processing relatively increase --

Column 15,
Line 16, change "costs. when" to -- costs. When --
Line 66, change "covalentlybonded." to -- covalently bonded --
Line 66, change "Whenonecycloalkyl group hastwoormore" to
-- When one cycloalkyl group has two or more --

Column 21,
Line 27, change "substitutedorunsubstitutedalkyl" to
-- substituted or unsubstituted alkyl --

Column 22,
Line 37, change "phoshorous" to -- phosphorous --

Column 23,
Line 7, change "vinirydene" to -- vinylidene --
Line 8, change "Inparticular" to -- In particular --

UNITED STATES PATENT AND TRADEMARK OFFICE
CERTIFICATE OF CORRECTION

PATENT NO. : 6,486,238 B1
DATED : November 26, 2002
INVENTOR(S) : Kitamura et al.

It is certified that error appears in the above-identified patent and that said Letters Patent is hereby corrected as shown below:

Column 27,
Line 9, change "modificatins" to -- modifications --

Column 42,
Line 26, change "polymnerizable" to -- polymerizable --

Column 44,
Line 6, change "(12)" to -- (11) --

Column 46,
Line 19, change "fiberprepared" to -- fiber prepared --.

Signed and Sealed this

Twenty-third Day of December, 2003

JAMES E. ROGAN
*Director of the United States Patent and Trademark Office*